United States Patent [19]

Becwar et al.

[11] Patent Number: 5,413,930
[45] Date of Patent: May 9, 1995

[54] METHOD FOR REGENERATION OF CONIFEROUS PLANTS BY SOMATIC EMBRYOGENESIS

[75] Inventors: Michael R. Becwar; Emily E. Chesick; Levis W. Handley, III, all of Charleston; Mark R. Rutter, Goose Creek, all of S.C.

[73] Assignee: Westvaco Corporation, New York, N.Y.

[21] Appl. No.: 138,994

[22] Filed: Oct. 21, 1993

[51] Int. Cl.⁶ ............................................. C12N 5/00
[52] U.S. Cl. ........................... 435/240.49; 435/240.5; 435/240.54
[58] Field of Search ..................... 435/240.46, 240.49, 435/240.5, 240.54

[56] References Cited

U.S. PATENT DOCUMENTS

| | | | |
|---|---|---|---|
| 4,957,866 | 9/1990 | Gupta et al. | 435/240.4 |
| 5,034,326 | 7/1991 | Pullman et al. | 435/240.4 |
| 5,036,007 | 7/1991 | Gupta et al. | 435/240.45 |
| 5,183,757 | 2/1993 | Roberts | 435/240.49 |
| 5,187,092 | 2/1993 | Uddin | 435/240.45 |

OTHER PUBLICATIONS

Nagmani, R., et al. Somatic embryogenesis in longleaf pine (*Pinus palustris*). *Canadian Journal of Forest Research* 23:873–876, 1993.

Becwar, M. R. et al. Initiation of embryogenic cultures and somatic embryo development in loblolly pine (*Pinus taeda*). *Canadian Journal of Forest Research* 20:810–817, 1990.

Etienne, H. et al. Water status of callus from *Hevea brasiliensis* during induction of somatic embryogenesis. *Physiologia Plantarum* 82:213–218, 1991.

Finer, J. J. et al. Initiation of embryogenic callus and suspension cultures of eastern white pine (*Pinus strobus* L.). *Plant Cell Reports* 8:203–206, 1989.

Grossnickle, S. C. et al. Integration of somatic embryogenesis in operational forestry: Comparison of interior spruce emblings and seedlings during production of 1+0 stock. In: Proceedings, Intermountain Forest Nursery Association. Aug. 12–16, 1991. Park City, Utah. USDA Forest Service, General Tech. Report RM-211. Pp. 106–113, 1992.

Gupta, P. K. et al. Shoot multiplication from mature trees of Douglas-fir (*Pseudotsuga menziesii*) and sugar pine (*Pinus lambertiana*). *Plant Cell Reports* 4:177–179, 1985.

Gupta, P. K. et al. Somatic polyembryogenesis from callus of mature sugar pine embryos. *Bio/Technology* 4:643–645, Jul. 1986.

Gupta, P. K. et al. Biotechnology of somatic polyembryogenesis and plantlet regeneration in loblolly pine. *Bio/Technology* 5:147–151, Feb. 1987.

Gupta, P. K. et al. Scale-up somatic embryogenesis of conifers for reforestation (Abstract). In: Proceedings, 3rd Inter. Assoc. of Plant Tissue Culture Canadian Workshop on Plant Tissue Culture and Genetic Engineering, Univ. of Guelph, Guelph, Ontario, Canada. Jun. 17–20, 1992.

Hakman, I. et al. Plantlet regeneration through somatic embryogenesis in *Picea abies* (Norway spruce). *Journal of Plant Physiology* 121:149–158, 1985.

Hakman, I. et al. The development of somatic embryos in tissue cultures initiated from immature embryos of *Picea abies* (Norway spruce). *Plant Science Ltrs* 38:53–59, 1985.

Harry I. S. et al. Somatic embryogenesis and plant regeneration from mature zygotic embroys of red spruce. *Botanical Gazette* 152:446–452, 1991.

(List continued on next page.)

*Primary Examiner*—David T. Fox
*Attorney, Agent, or Firm*—Daniel B. Reece, IV; Terry B. McDaniel; Richard L. Schmalz

[57] ABSTRACT

This invention relates to a method for regeneration of coniferous plants. In particular, this invention relates to the development of a multi-step method that is able to complete the entire somatic embryogenesis regenerative process, from explant collection to planting, for plants of the genus Pinus and Pinus interspecies hybrid plants. This method is well suited for producing clonal planting stock useful for reforestation.

32 Claims, 4 Drawing Sheets

OTHER PUBLICATIONS

Jain, S. M. et al. Somatic embryogenesis in slash pine (*Pinus elliottii*) form immature embryos cultured in vitro. *Plant Science* 65:233–241, 1989.

Kermode, A. R. et al. The role of maturation drying in the transition from seed development to germination. *Journal of Experimental Botany* 36:1906–1915, Dec. 1985.

Kermode, A. R. et al. The role of maturation drying in the transition from seed development to germination. *Journal of Experimental Botany* 40:303–313, Feb. 1989.

Klimaszewska, K. Plantlet development from immature zygotic embryos of hybrid larch through somatic embryogenesis. *Plant Science* 63:95–103, 1989.

Klimaszewska, K. et al. Cryopreservation and plant regeneration from embryogenic cultures of larch (*Larix x eurolepis*) and black spruce (*Picea marina*). *Journal of Experimental Botany* 43:73–79, Jan. 1992.

Laine, E. et al. Somatic embryogenesis in immature embryos and protoplasts of *Pinus caribaea*. *Plant Science* 69:215–224, 1990.

Michler, C. H. et al. Effects of embryo explant type and developmental maturity on eastern white pine (*Pinus strobus* L.) embryogenic callus initiation (Abstract). In: Applications of biotechnology to tree culture, protection and utilization. (eds. Haissig et al.) Columbus, Ohio. Aug. 5–8, 1991. USDA Forest Serv., Northeastern Forest Expt. Station, p. 117, 1991.

Owens, L. D. et al. Measurement and effects of gel matric potential and expressibility on production of morphogenic callus by cultured sugarbeet leaf discs. *Plant Cell, Tissue and Organ Culture* 26:127–133, 1991.

Preston, J. R. North American Trees, 4th edition. Iowa State Univ. Press, Ames, pp. 4–7, 1989.

Schenk, R. U. et al. Medium and techniques for induction and growth of monocotyledonous and dicotyledonous plant cell cultures. *Canadian Journal of Botany* 50:199–204, 1972.

Smith, D. R. et al. Zygotic embryos of *Pinus radiata* in vivo and in vitro. In: Smith D R (ed) Abstracts, Int. Conifer tissue culture working group, 12–16 Aug. 1985, Forest Research Institute, N Z For Serv, Rotorua, New Zealand, 1985.

Tautorus, T. E. et al. Somatic embryogenesis in conifers. *Canadian Journal of Botany* 69:1873–1899, 1991.

Teasdale, R. D. et al. Mineral nutrient requirements of a loblolly pine (*Pinus taeda*) cell suspension culture. *Plant Physiology* 82:942–945, 1986.

Tremblay, L. et al. Effects of gelling agents, ammonium nitrate, and light on the development of *Picea mariana* (Mill) B. S. P. (black spruce) and *Picea rubens* Sarg. (red spruce) somatic embryos. *Plant Science* 77:233–242, 1991.

von Arnold, S. Improved efficiency of somatic embryogenesis in mature embryos of *Picea abies* (L.) Karst. *Journal of Plant Physiology* 128:233–244, 1987.

von Arnold, S. et al. Regulation of somatic embryo development in *Picea abies* by abscisic acid (ABA). *Journal of Plant Physiology* 32:164–169, 1988.

Webster, F. B. et al. Propagation of interior spruce by somatic embryogenesis. *Canadian Journal of Forest Research* 20:1759–1765, 1990.

Becwar, M. R. et al. Development and characterization of in vitro embryogenic systems in conifers. In Ahuja MR (ed) Somatic Cell Genetics of Woody Plants, pp. 1–18, 1988.

Seed Culture B19

Seed Source A45 X A33/38

Seed Source A45 X A26

Seed Source A10

METHOD FOR REGENERATION OF CONIFEROUS PLANTS BY SOMATIC EMBRYOGENESIS

FIELD OF INVENTION

This invention relates to a method for regeneration of coniferous plants. In particular, this invention relates to the development of a multi-step method that is able to complete the entire somatic embryogenesis regenerative process, from explant collection to field planting, for plants of the genus Pinus and Pinus interspecies hybrid plants. This novel method is well suited for producing clonal planting stock useful for reforestation.

BACKGROUND OF THE INVENTION

Reforestation, the controlled regeneration of forests, has become an integral part of forest management in order to secure a renewable and sustainable source of raw material for production of paper and other wood-related products. Forest trees can be regenerated by either sexual or asexual propagation. Sexual reproduction of seedlings for reforestation has traditionally been the most important means of propagation, especially with coniferous species.

Tree improvement programs with economically important conifers (e.g., Pinus, Picea, and Pseudotsuga species) have applied genetic principles of selection and breeding to achieve genetic gain. Based on the results of progeny tests, superior maternal trees are selected and used in "seed orchards" for mass production of genetically improved seed. The genetic gain in such an open-pollinated sexual propagation strategy is, however, limited by the breeder's inability to control the paternal parent. Further gains can be achieved by control-pollination of the maternal tree with pollen from individual trees whose progeny have also demonstrated superior growth characteristics. Yet sexual propagation results in a "family" of seeds comprised of many different genetic combinations (known as siblings), even though both parents of each sibling seed are the same. As not all genotype combinations are favorable, the potential genetic gain is reduced due to this genetic variation among sibling seeds.

In addition to these genetic limitations, large-scale production of control pollinated seeds is expensive. These economic and biological limitations on large-scale seed production have caused considerable interest to develop in the industry for applying asexual methods to propagate economically important conifers.

The use of asexual propagation permits one to apply what is known as a very high selection intensity (that is, propagate only progeny showing a very high genetic gain potential). These highly desirable progeny have unique genetic combinations that result in superior growth and performance characteristics. Thus, with asexual propagation it is possible to multiply genetically select individuals while avoiding a concomitant reduction of genetic gain due to within family variation.

Asexual propagation of trees can be accomplished by methods of grafting, vegetative propagation, and micropropagation. Grafting, widely used to propagate select individuals in limited quantities for seed orchard establishment, is not applicable to large-scale production for reforestation. Vegetative propagation by rooting of cuttings and micropropagation by somatic embryogenesis currently hold the most potential for reforestation of coniferous trees. Although vegetative propagation by rooted cuttings can be achieved in many coniferous species, large-scale production via this method is extremely costly due to difficulties in automating and mechanizing the process. This propagation method is further limited by the fact that the rooting potential of stock plants decrease with time, making it difficult to serially propagate from select genotypes over extended periods of time.

Micropropagation by somatic embryogenesis refers to methods whereby embryos are produced in vitro from small pieces of plant tissue or individual cells. The embryos are referred to as somatic because they are derived from the somatic (vegetative) tissue, rather than from the sexual process. Both vegetative propagation and micropropagation have the potential to capture all genetic gain of highly desirable genotypes. However, unlike conventional vegetative propagation methods, somatic embryogenesis is amenable to automation and mechanization, making it highly desirable for large-scale production of planting stock for reforestation. In addition, somatic embryogenic cultures can easily be preserved in liquid nitrogen. Having a long-term cryogenic preservation system offers immense advantages over other vegetative propagation systems which attempt to maintain the juenility of stock plants.

The current invention specifically relates to the development of an improved cell and tissue culture system for micropropagation of conifers by somatic embryogenesis. It was not until 1985 that somatic embryogenesis was discovered in conifers (Hakman et al. 1985) and the first viable plantlets were regenerated from conifer somatic embryos (Hakman and von Arnold 1985). Since 1985 conifer tissue culture workers throughout the world have pursued the development of somatic embryogenesis systems capable of regenerating plants. The goal of much of this work is to develop conifer somatic embryogenesis as an efficient micropropagation system for producing clonal planting stock enmasse. In addition, the embryogenic micropropagation system interfaces very well with genetic engineering techniques for production of transgenic clonal planting stock of conifers.

The two most economically important conifer genera are Picea (spruce) and Pinus (pine). There are about 30 species of Picea, largely restricted to cooler regions of the northern hemisphere, of which seven species are native to North America. Pinus is the largest and most important genus of conifers, having approximately 95 species scattered over the northern hemisphere. Of these 95 species, 36 are native to North America. (Preston 1989).

Those working in conifer somatic embryogenesis have found that there is a striking difference between Picea conifers and Pinus conifers as to the ease with which somatic embryogenesis can be induced and plants regenerated (Tautorus et al. 1991). Indeed, if one evaluates the success of somatic embryogenesis in conifers among species of these two important genera, it is clear that much more success has been achieved with Picea than with Pinus. It is also striking how consistent the success on developing somatic embryogenic systems has been among several Picea species, whereas the recalcitrance of Pinus has been equally consistent across several species.

Progress in somatic embryogenesis can in part be evaluated by the level of success in three important steps of the process: (1) initiation of embryogenic cultures, (2) production of fully developed somatic embryos, and (3) establishment of somatic embryo plants under field conditions. Among Picea species embryogenic culture initiation frequencies are relatively high; as high as 95% from immature zygotic embryos, and as high as 55% from mature zygotic embryos harvested from fully developed, dry seeds (Tautorus et al. 1991). There are numerous reports of production of fully developed somatic embryos among Picea species, and several reports of establishment and growth of Picea somatic embryo plants in soil. Researchers at the British Columbia Research Corporation have reported on establishment of interior spruce (a mixture of *Picea glauca* and *Picea englemannii*) somatic embryo plants under nursery conditions. For example, Webster et al. (1990) reported over 80% survival and establishment in nursery conditions of interior spruce somatic embryo plants for most of 71 genotypes tested. Grossnickle et al. (1992) reported the establishment of 40% of 2000 interior spruce somatic embryo plants in nursery conditions. The somatic embryo plants were derived from 15 different genotypes. Researchers at the Weyerhaeuser Corporation have reported similar success with Norway spruce (*Picea abies*); over 3000 somatic embryo plants from 17 genotypes have been established in the field (Gupta et al. 1992). Similar success was also reported with Douglas-fir (*Pseudotsuga menziesii*); over 2000 somatic embryo plants from 6 genotypes of have been established in soil in greenhouse conditions. Thus, conifer somatic embryogenesis workers utilizing Picea species (and commercially important Douglas-fir) have been successful in developing culture initiation and regeneration systems that enable relatively routine production of plants capable of transfer to field conditions. The rapid successes in Picea somatic embryogenesis had lead to considerable optimism among researchers that commercial utilization of conifer somatic embryogenesis for production of clonal planting stock of Pinus conifers would be readily achievable.

However, the progress achieved with somatic embryogenesis in Pinus species to date has been much less encouraging than that achieved with Picea species. First and foremost in difficulty is the recalcitrance of Pinus species for initiation of embryogenic cultures. For example, initiation frequencies of about 1 to 5% are routinely cited by those working with Pinus species (Gupta and Durzan 1987, Becwar et al. 1988, Jain and Newton 1989, Becwar et al. 1990). The single report claiming a 54% initiation rate from immature zygotic embryos of *Pinus strobus* (Finer et al. 1989) has yet to be repeated or duplicated by others working with this species (Michler et al. 1991). Secondly, it is extremely difficult to obtain reliable development of Pinus somatic embryos to the fully developed (cotyledonary) stage. In addition, subsequent production of plantlets has been extremely limited in Pinus species. Tautorus et al. (1992) cited only 3 of 7 reports which indicated plantlets were obtained via somatic embryogenesis in Pinus species. (In contrast, 30 of 43 reports with Picea species reported obtaining plantlets via somatic embryogenesis.) Unlike the reports with Picea species where several systems have shown potential for plantlet production on relatively large scales, the reports of plantlet production from Pinus species have yielded few plants. To our knowledge there is only one report of successful establishment of Pinus somatic embryos in soil (Gupta and Durzan 1987). The authors of this report have had limited success in obtaining *Pinus taeda* somatic embryo plants . . . , indeed, only one culture genotype was taken to the plantlet stage and only one plant was transferred to soil (see Pullman and Gupta 1991). To date the only published report of higher numbers of germination of Pinus somatic embryos is for *Pinus caribaea*, where 34 of 69 (49%) germinated (Laine and David 1990). However, the authors did not report establishment of these plants in field conditions. Thus, for Pinus species all three integral parts of the somatic embryogenesis process have not progressed to the stages currently achieved with Picea.

Having a low initiation frequency can severely limit the potential applications of somatic embryogenesis in Pinus species for large scale production of genetically improved conifers for he following reason. Skilled artisans in the field of conifer tissue culture recognize that the use of embryogenic cultures derived from juvenile explants (e.g., zygotic embryos derived from seed) necessitate that the resulting regenerated plants be field tested prior to large scale production. Only selected genotypes which show the potential for producing significant genetic gain in such a field test will subsequently be propagated by somatic embryogenesis. Therefore it will be necessary to screen numerous genotypes from desirable parents, initiate embryogenic cultures, cryopreserve each genetically different culture, regenerate plants from each genetically different culture, field test plants from each genotype, and choose select genotypes for large scale production via somatic embryogenesis. Low culture initiation frequencies pose severe limitations for implementing this strategy. Indeed, an unbeknownst selection process may occur when low initiation frequencies exclude a majority of the genotypes. In the case of Pinus species where initiation frequencies are very low (e.g., 1 to 5%) one could be selecting for embryogenic potential, but selecting against improved growth potential (which may be in the 95 to 99% of the genotypes eliminated as non-embryogenic). The potential problem of eliminating desirable genotypes is exacerbated by the exceedingly low initiation frequencies among Pinus species. By contrast, with Picea species where initiation frequencies are much higher (approaching 100% from immature zygotic embryos of some Picea species) it is much less likely that one will eliminate by selection those genotypes which have superior growth potential.

One component of an efficient somatic embryogenesis regeneration system is the culture medium. Semisolid culture media are routinely used during the culture initiation, the culture maintenance, and the embryo development phases. The culture medium is generally composed of six groups of ingredients: inorganic nutrients, vitamins, organic supplements, a carbon source, phytohormone(s), and a gelling agent for semisolid media. The two gelling agents usually employed for conifer somatic embryogenesis are agar and gellan gum, with agar being most commonly used.

Gelling agent concentration and type are known to influence growth responses of certain non-coniferous plant tissue cultures, but the effects of gelling agent concentration are varied and complex among different plant species and plant tissue types. For example, in a study working with rose (*Rosa hybrida*) tissue cultures Ghashghaie et al. (1991) found that increasing the availability of water by lowering a medium's agar concentration increased shoot elongation, yet did not improve shoot multiplication. Etienee et al. (1991) showed that culturing rubber tree (*Hevea brasiliensis*) explants on cellulose blocks in liquid medium increased embryogenic tissue initiation in comparison to culturing on the same medium gelled with a standard level of 2 grams of GELRITE® (gellan gum manufactured by Merck, Inc.) per liter of medium (grams/liter or g/l). They suggested the increased initiation was due to increased water availability of the liquid medium relative to the gelled medium. But, they did not determine if culturing explants on medium gelled with low levels of GELRITE (e.g, 1 g/l) similarly increased initiation. In another study utilizing sugarbeet (*Beta vulgaris*) leaf discs, Owens and Wozniak (1991) obtained more somatic embryos and shoots from leaf discs cultured on low levels of gelling agent. However, their results were obtained from sugarbeet explants cultured on a filter-paper overlay. The study did not directly evaluate how varying gelling agent concentration effected somatic embryo production from sugarbeet explants cultured directly on the culture medium surface.

Those working in the field of conifer somatic embryogenesis have mainly emphasized medium components other than the gelling agent in attempts to improve culture initiation or development of somatic embryos (Tautorus et al. 1991). Only four reports have examined the effect of gelling agents on conifer somatic embryogenesis (von Arnold 1987, Klimaszewska 1989, Harry and Thorpe 1991, and Tremblay and Tremblay 1991). In her study von Arnold (1987) compared agar to GELRITE and found no difference between the two gelling agents for initiation of embryogenic tissue from mature zygotic embryos of *Picea abies*. The study did not test media gelled with levels of agar and GELRITE below 7 and 2 g/l, respectively. Klimaszewska (1989) compared the effect of agar versus GELRITE on proliferation and growth of Larix embryogenic cultures. Cultures initiated on medium gelled with 7 g/l of agar proliferated and grew best when transferred to medium gelled with 4 g/l of GELRITE. Although her study did not examine the effects of low levels of gelling agents on culture initiation, she noted that it was difficult to maintain high quality cultures on a medium containing a low level of GELRITE (1 g/l). Harry and Thorpe (1991) tested the effect of agar and GELRITE concentration on initiation of *Picea rubens* embryogenic tissue, but did not test levels below 6 and 2 g/l, respectively. Tremblay and Tremblay (1991) examined the effect of gelling agents on the development of *Picea abies* and *Picea rubens* somatic embryos. They found that GELRITE was superior to agar, in that 3 to 5 times more somatic embryos developed on medium gelled with GELRITE than with agar. But, similar to the above three studies, concentrations of agar and GELRITE below 7 and 2 g/l, respectively, were not tested.

Researchers in conifer somatic embryogenesis have commonly employed the same levels of gelling agents typically used in other plant cell and tissue culture research. These traditional gelling agent levels are 6.0 to 9.0 grams of agar per liter of medium, 2.0 to 4.0 g/l of gellan gum (or GELRITE), 6.0 to 10.0 g/l of agarose (a purified form of agar), and 3.5 to 5.0 g/l of AGARGEL® (an agar/gellan gum mixture manufactured by Sigma Chemical Co.). Although Hakman et al. (1985) employed an agar level of 5 g/l in a study to induce somatic embryogenic cultures of *Picea abies*, no suggestion was made by the authors of any significance or advantage to using this level. Indeed, in subsequent studies these authors exclusively used higher levels of GELRITE (3 to 4 g/l) (Hakman and von Arnold 1985, von Arnold and Hakman 1988). To our knowledge, no one heretofore has explored the efficacy of using low levels of gelling agents for somatic embryogenesis among conifers.

The implementation of somatic embryogenesis in Pinus species for production of clonal planting stock is also severely limited by the lack of a reproducible multistep regeneration system. Very few laboratories working with Pinus have effectively produced embryogenic cultures or even produced cotyledonary stage somatic embryos. Even fewer workers have regenerated Pinus plants by somatic embryogenesis (Tautorus et al. 1991). In the cases where plants have been regenerated from Pinus embryogenic cultures, both the number of responsive culture genotypes and the number of plants obtained have been very low.

The present invention is a multi-step somatic embryo regeneration method that is applicable to Pinus species and has demonstrated potential to regenerate plants from a diverse range of culture genotypes. The invention method also improves the embryogenic culture initiation frequency. This in itself is highly significant because it ensures that more embryogenic cultures survive to the culture maintenance phase, thereby allowing more genotypes to be subsequently available for field testing and production of clonal planting stock.

In U.S. Pat. No. 4,957,866, Gupta et al. teach a process for reproducing coniferous plants (i.e. *Pinus taeda*) via somatic embryogenesis. Direct comparisons were performed between the patented process and the method taught in the present invention (see Examples 5 and 7 below). The results contained in Example 5 clearly showed that the current invention method provides a significant improvement in culture initiation when compared to the Gupta et al. process. (As noted above, it is vitally important to improve the culture initiation method practiced with Pinus in order to assure that more embryogenic culture genotypes are initiated and available for use in subsequent steps of the regeneration method.) In Example 7 the process of increasing the predevelopment medium osmotic potential disclosed in the Gupta et al. patent was compared to the method taught in the current invention. There the results achieved across several culture genotypes were at least equivalent, and in most cases far better, using the method of the current invention.

In U.S. Pat. No. 5,034,326, Pullman and Gupta teach a process for reproducing coniferous plants (i.e. *Pinus taeda*) via somatic embryogenesis which involves using activated carbon and high levels of abscisic acid in the embryo development medium. In Example 6 the use of high levels of abscisic acid and activated carbon in embryo development medium as disclosed by the Pullman and Gupta patent was compared to the method taught in the current invention. This comparison study found the method taught in the current invention to be very effective while, in contrast, the patented process was found to be ineffective.

In U.S. Pat. No. 5,036,007, Gupta and Pullman teach a process for reproducing coniferous plants via somatic embryogenesis which involves using abscisic acid and osmotic potential variation of the culture medium. In addition to utilizing high levels of abscisic acid in combination with activated carbon, they also teach using a subsequent embryo development medium having very high osmolality levels (preferably in the range of about 450 mM/kg). The current invention differs significantly from both of the above patented processes (U.S. Pat.

Nos. 5,034,326 and 5,036,007). First, in the current invention activated carbon is not used in combination with abscisic acid. Second, the current invention does not require the embryo development medium to have the high osmolality levels as taught by Gupta and Pullman (1991).

Therefore, an object of the present invention is to provide a method for mass producing clones of Pinus conifers by the process of somatic embryogenesis.

Another object of the present invention is an improved embryogenic culture initiation method for Pinus conifers.

A further object of the present invention is to provide a multistage regeneration protocol which can be utilized effectively on Pinus conifers to produce large quantities of plants for field planting.

Another object of the present invention is to provide a progression of steps which, in combination, enable one to complete the somatic embryo regeneration method on a number of diverse genotypes of *Pinus taeda* and other *Pinus species*.

In addition, it is the object of the present invention to provide a progression of steps which, in combination, enable one to complete the somatic embryo regeneration method on a number of diverse genotypes of Pinus interspecies hybrids (e.g., *Pinus taeda* × *Pinus rigida*).

SUMMARY OF THE INVENTION

These objectives are achieved by a multi-step method for the regeneration of Pinus conifer plants by somatic embryogenesis. Although other somatic embryogenesis regeneration protocols for conifers have been published, none of these methods have proven totally effective with the Pinus species in that none enabled the practitioner to reliably proceed from the beginning step of explant collection to completion of the regeneration process resulting in establishment of plants in field conditions. Our invention provides such a multi-step method for Pinus conifer plants.

There are several advantages inherent with the use of this novel method. For example, the method is well suited for large-scale production of clonal planting stock of Pinus conifer plants. In addition, the method interfaces very well with genetic engineering techniques for mass production of clones of genetically modified and improved Pinus trees.

The method also results in an improved embryogenic culture initiation frequency which allows more vigorous cultures to be obtained (which can be successfully carried through subsequent stages of the regeneration process). Furthermore, the method makes it feasible to include more genotypes in subsequent clonal field tests and thereby increase the likelihood of being able to select highly productive genotypes. Also, more culture genotypes can be quickly proliferated via this method for rapid production of clonal planting stock from selected parents.

The present invention also provides a reliable multi-step regeneration method for the recalcitrant Pinus species. It is the combined application of the progression of steps in this novel multi-step method that has enabled the first successful field planting of many different genotypes of Pinus somatic embryos.

BRIEF DESCRIPTION OF THE DRAWINGS

The figures illustrate some of the results obtained in Example 1 (which demonstrated an effective multi-step method for the regeneration of *Pinus taeda L.* by somatic embryogenesis) and Example 4 (which compared the present method with the process taught by Gupta and Pullman in U.S. Pat. No. 4,957,866—particularly the method of initiating the embryogenic culture as taught in Step 2 of Example 1 of the present method).

DESCRIPTION OF THE PREFERRED EMBODIMENT

Figure 1:
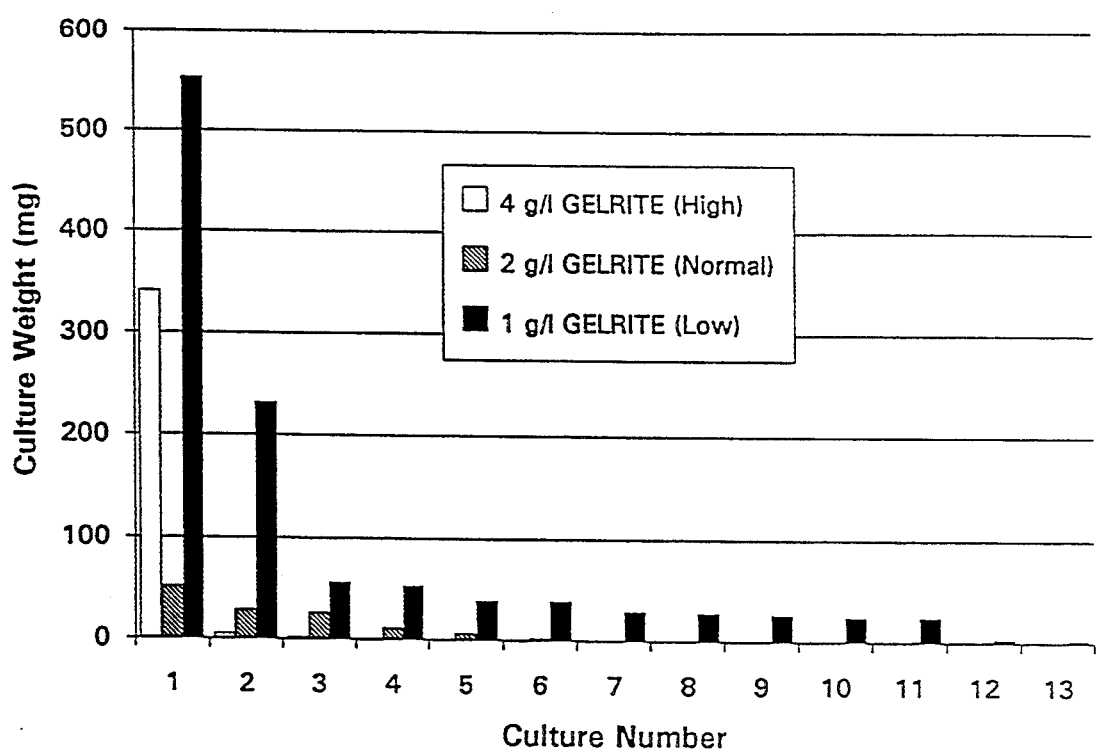
FIG. 1 shows the effect of gelling agent concentrations on culture initiations for seed source B19.

The present invention, a multi-step method for the regeneration of plants of the genus Pinus and Pinus interspecies hybrid plants by somatic embryogenesis, generally comprises the following sequential steps:

1. placing a suitable explant on culture initiation medium containing a sufficient amount of nutrients and plant growth hormones, and a level of gelling agent selected from the group consisting of 2.5 to 4.5 g/l of agar, 0.5 to 1.5 g/l of gellan gum, 3.0 to 5.0 g/l of agarose, and 1.5 to 3.0 g/l of AGARGEL, for 2 to 14 weeks under suitable environmental conditions to grow a culture containing embryogenic tissue;

2. transferring the embryogenic tissue culture to culture maintenance medium having a sufficient amount of nutrients and plant growth hormones, and a level of gelling agent selected from the group consisting of 6.0 to 9.0 g/l of agar, 1.75 to 3.50 g/l of gellan gum, 6.0 to 8.0 g/l of agarose, and 3.5 to 5.0 g/l of AGARGEL, for a sufficient time under suitable environmental conditions to develop a mass of embryogenic tissue having a minimum weight of 100 mg;

3. transferring at least 100 mg of the mass of embryogenic tissue to embryo development medium containing a sufficient amount of nutrients, 5 to 33 mg/l of abscisic acid, a level of gelling agent selected from the group consisting of 6.0 to 12.0 g/l of agar, 1.75 to 4.00 g/l of gellan gum, 6.0 to 8.0 g/l of agarose, and 3.5 to 6.0 g/l of AGARGEL, and 20.0 to 150.0 g/l of a sugar selected from the group consisting of glucose, maltose, sucrose, and combinations thereof for a sufficient time under suitable environmental conditions to develop stage 3 somatic embryos;

4. separating the stage 3 somatic embryos from the development medium and partially drying the embryos by exposing the embryos to an atmosphere having a high relative humidity (about 99%) for sufficient time to permit the embryos to lose about 25% to 75% of their pre-dried weight;

5. transferring the partially dried somatic embryos to germination medium containing a sufficient amount of nutrients, a level of gelling agent selected from the group consisting of 6.0 to 9.0 g/l of agar, 1.75 to 3.50 g/l of gellan gum, 6.0 to 8.0 g/l of agarose, and 3.5 to 5.0 g/l of AGARGEL, and 20.0 to 40.0 g/l of a sugar selected from the group consisting of glucose, maltose, sucrose, and combinations thereof for a sufficient time under suitable environmental conditions to germinate the partially dried embryos;

6. converting the germinated embryos into acclimatized somatic embryo plants; and 7. field planting the acclimatized somatic embryo plants.

This method is generally applicable to somatic tissue obtained from the Pinus species including, but not limited to, the following: Pinus taeda (loblolly pine), P. elliottii (slash pine), P. palustris (longleaf pine), P. serotina (pond pine), P. echinata (shortleaf pine), P. clausa (sand pine), P. glabra (spruce pine), P. rigida (pitch pine), P. echinata (shortleaf pine), P. nigra (Austrian pine), P. resinosa (red pine), P. sylvestris (Scotch pine), P. pungens (Table Mountain pine), P. banksiana (jack pine), P. virginiana (Virginia pine), P. radiata (Monterey pine), P. banksiana (jack pine), P. contorta (shore pine), P. contorta latifolia (lodgepole pine), P. ponderosa (ponderosa pine), P. ponderosa arizonica (Arizona pine), P. torreyana (Torrey pine), P. coulteri (Coulter pine), P. sabiniana (digger pine), P. muricata (bishop pine), P. attenuata (knobcone pine), P. leiophylla (Chihuahua pine), P. washoensis (Washoe pine), P. jeffreyi (Jeffrey pine), and P. engelmannii (Apache pine); and soft pines including Pinus strobus (eastern white pine), P. monticola (western white pine), and P. lambertiana (sugar pine), P. albicaulis (whitebark pine), P. flexilis (limber pine), P. strobiformis (southwestern white pine), P. aristata (bristlecone pine), P. balfouriana (foxtail pine), P. monophylla (singleleaf pine), P. edulis (pinyon), P. cembroides (Mexican pinyon), P. quadrifolia (Parry pinyon) and P. caribaea (caribbean pine). In addition, the current invention is specifically applicable to interspecies hybrids of the above mentioned pines including Pinus rigida $\times$ P. taeda, P. serotina $\times$ P. taeda, and reciprocal crosses.

Any somatic tissue explant capable of being employed for somatic embryogenesis is suitable for use in present method. However, it is preferred that the explant be either an immature whole megagametophyte containing zygotic embryos or an isolated immature dominant zygotic embryo.

The method of the present invention is not limited to any single culture nutrient medium formulation. For example, the basal culture media formulations used in Examples 1–10 are listed in Table I below; while other specific media formulations employed in Examples 1–10 are listed in Table II below.

TABLE I

| Formulations Of Basal Culture Media | | |
|---|---|---|
| COMPONENT | DCR[a] | MSG[b] |
| | CONCENTRATION, mg/l | |
| INORGANIC SALTS | | |
| NH$_4$NO$_3$ | 400.00 | — |
| KNO$_3$ | 340.00 | 100.00 |
| Ca(NO$_3$)$_2$.4H$_2$O | 556.00 | — |
| MgSO$_4$.7H$_2$O | 370.00 | 370.00 |
| KH$_2$PO$_4$ | 170.00 | 170.00 |
| CaCl$_2$.2H$_2$O | 85.00 | 440.00 |
| KCl | — | 745.00 |
| KI | 0.83 | 0.83 |
| H$_3$BO$_3$ | 6.20 | 6.20 |
| MnSO$_4$.H$_2$O | 22.30 | 16.90 |
| ZnSO$_4$.7H$_2$O | 8.60 | 8.60 |
| Na$_2$MoO$_4$.2H$_2$O | 0.25 | 0.25 |
| CuSO$_4$.5H$_2$O | 0.25 | 0.03 |
| CoCl$_2$.6H$_2$O | 0.03 | 0.03 |
| NiCl$_2$.6H$_2$O | 0.03 | — |
| FeSO$_4$.7H$_2$O | 27.80 | 27.80 |

TABLE I-continued

| Formulations Of Basal Culture Media | | |
|---|---|---|
| COMPONENT | DCR[a] | MSG[b] |
| | CONCENTRATION, mg/l | |
| Na$_2$EDTA | 37.30 | 37.30 |
| VITAMINS, AMINO ACID | | |
| Nicotinic acid | 0.50 | 0.50 |
| Pyridoxine.HCl | 0.50 | 0.10 |
| Thiamine.HCl | 1.00 | 0.10 |
| Glycine | 2.00 | — |

[a]According to Gupta and Durzan (1985)
[b]According to Becwar et al. (1990)

TABLE II

| Composition Of Media Commonly Used In The Examples Below | | | | |
|---|---|---|---|---|
| COMPONENT | Initiation/maintenance medium DCR$_1$ | Pre-development medium MSG$_1$ | Development medium KSG$_2$ | Germination medium KSG$_3$ |
| Basal medium[a] | DCR | MSG | MSG | MSG |
| | | CONCENTRATION, g/l | | |
| Inositol | 0.50 | 0.10 | 0.10 | 0.10 |
| Casein hydrolysate | 0.50 | — | — | — |
| L-glutamine | 0.25 | 1.45 | 1.45 | 1.45 |
| Sucrose | 30.00 | 30.00 | — | 30.00 |
| Maltese | — | — | 60.00 | — |
| Agar | — | 8.00 | — | 8.00 |
| GELRITE | Int: 1.00 Mnt: 2.00 | — | 2.00 | — |
| Activated carbon | — | 5.00 | — | 5.00 |
| Auxin[b] | 3.00 | — | — | — |
| Cytokinin[c] | 0.50 | — | — | — |
| ABA[d] | — | — | 11.00–22.00 mM/kg | — |
| Medium osmolality | 145–155 | 145–165 | 250–260 | 145–165 | a) Refer to Table I for composition of basal medium.
b) 2,4-dichlorophenoxyacetic acid (2,4-D).
c) N[6]-benzylaminopurine [or N[6]-benzyladenine (BA)].
d) Abscisic acid Gelling agents which are suitable for use in the present method include, but are not limited to, the following: agar, gellan gum, agarose (a purified form of agar), and mixtures thereof (e.g. AGARGEL® an agar/gellan gum mixture purchased from Sigma Chemical Co.).

As noted above, heretofore no one has explored the efficacy of using low levels of gelling agents for somatic embryogenesis among the more recalcitrant Pinus species. The results of our experiments showed that gelling agent concentration has a profound effect on both the extrusion and the initial proliferation of embryogenic tissue.

Two parameters characterize the availability of water in a gelled medium: (1) gel matric potential—the tenacity with which water is held by the solid phase of the gel, and (2) gel expressability—the ease with which water is expressed in response to mechanical deformation of the gel. At lower concentrations of gelling agents more water is available to plant tissue cultures because the water is held less tenaciously by the gel and the water is expressed more easily by contact of the explant to the medium (gel) surface.

The osmolality of DCR$_1$ medium containing different types and levels of gelling agents were measured by inserting paper discs into gelled medium for 30 seconds, then placing the discs in a vapor pressure osmometer (Model 5500 manufactured by Wescor, Inc.). Control measurements of medium containing no gelling agents (liquid medium) were taken by loading 10 μl of liquid on paper discs. The results are listed in Table III below.

TABLE III

Osmolality Of DCR₁ Medium Containing Different Types And Levels of Gelling Agents.

| Gelling Agent | | Medium Osmolality (mmol/kg) |
|---|---|---|
| Type | Conc. (g/l) | mean ± st. error[a] |
| GELRITE | 1 | 124 ± 5 |
| | 2 | 127 ± 2 |
| | 4 | 130 ± 6 |
| Agar | 4 | 135 ± 4 |
| | 8 | 157 ± 2 |
| | 12 | 165 ± 3 |
| Agarose | 4 | 138 ± 3 |
| | 6 | 136 ± 1 |
| | 8 | 137 ± 1 |
| None[b] | 0 | 121 ± 4 |

[a]Mean of three measurements.
[b]Liquid DCR₁ medium.

Measurements of medium osmotic potential (osmolality) showed very little change with changing concentrations of GELRITE and agarose. Osmolality levels of media gelled with GELRITE, regardless of the GELRITE concentration, were similar to liquid medium containing no gelling agent. Medium gelled with agarose had slightly higher osmolality levels than medium gelled with GELRITE, but osmolality did not change appreciably with increasing agarose. Increasing the agar concentration resulted in somewhat increased osmolality levels, unlike the other two gelling agents. However, based on these measurements it is not likely that differential response of explants cultured on different levels of these gelling agents can be attributed to osmotic effects.

These and other results suggest that the positive effect of lower gelling agent concentration is due to increased water availability, rather than a specific effect of the type of gelling agent. However, one can not rule out the possibility that the positive effect of the lower levels of gelling agents is due to decreased exposure to inhibitory substances (impurities) in the gelling agents. Furthermore, ion availability also appears to be dependent on gelling agent concentration and may, therefore, be a factor contributing to the positive effect of lower gelling agent concentration.

Thus, a key feature of our multi-step method is the use of low levels of gelling agents during culture initiation (see Step 2 of Example 1). Specifically, our method is practiced by utilizing culture initiation medium containing a level of gelling agent including 2.5 to 4.5 g/l of agar, 0.5 to 1.5 g/l of gellan gum. 3.0 to 5.0 g/l of agarose, or 1.5 to 3.0 g/l of AGARGEL. The preferred gelling agent levels are 3.0 to 4.0 g/l of agar, 0.75 to 1.25 g/l of gellan gum, 3.5 to 4.5 g/l of agarose, or 1.75 to 2.50 g/l of AGARGEL. The common practice in the field of plant tissue culture is to use higher levels of gelling agents than we have found beneficial for Pinus culture initiation. Indeed, heretofore no one has shown or even suggested that using lower than normal levels of gelling agents is highly advantageous in initiating conifer embryogenic tissue cultures.

Culture initiation lasts for a period of from 2 to 14 weeks, with the preferred period being 3 to 10 weeks. After this period of time the embryogenic tissue is transferred for further proliferation and maintenance to culture maintenance medium containing a higher level of gelling agent. Levels of gelling agents which are suitable for use in this method in the culture maintenance medium (as well as the germination medium and, if employed, the predevelopment medium) include the following: 6.0 to 9.0 g/l of agar, 1.75 to 3.50 g/l of gellan gum, 6.0 to 8.0 g/l of agarose, and 3.5 to 5.0 g/l of AGARGEL. The embryogenic tissue is maintained on this medium until a mass of embryogenic tissue having a minimum weight of about 100 mg has developed (a period of about 1 to 14 weeks).

While one may practice the present method without utilizing auxin (e.g., 2,4-dichlorophenoxy acetic acid) or cytokinin (e.g., $N^6$-benzyladenine) in either the culture initiation medium or the culture maintenance medium, it is preferred to incorporate each of them into both media. Suitable levels for the present method include about 0.1 to 5.0 mg/l for auxin and about 0.1 to 1.0 mg/l for cytokinin.

The embryogenic tissue can be maintained by subculturing at regular intervals (usually every 2 to 3 weeks) to new maintenance medium. Alternatively, embryogenic tissue can be placed in liquid culture medium and grown as a liquid embryogenic suspension (as shown in Example 4 below). Embryogenic tissue cultures maintained either on semi-solid maintenance medium or in liquid suspension can be cyropreserved via standard techniques for future use (as shown in Example 8 below).

After the mass (or masses) of embryogenic tissue has proliferated sufficiently such that the culture can be maintained, a tissue mass of at least 100 mg (preferably at least 200 mg) is transferred to embryo development medium for a period of time sufficient to develop stage 3 embryos (usually a period of about 3-18 weeks). It should be noted that the present method may be practiced by utilizing more than one mass of embryogenic tissue. Of course, for large scale production numerous masses would be utilized.

The development medium suitable for use in the present method contains a sufficient amount of nutrients, about 20.0 to 150.0 g/l of sugar selected from the group consisting of glucose, maltose, sucrose, and combinations thereof, and abscisic acid (ABA) in an amount ranging from 5 to 33 mg/l. The preferred amount of sugar for use in the development medium ranges from about 20 to 70.0 g/l, while the preferred sugar is maltose. The preferred osmolality range is from about 120 to 330 mM/kg. The preferred range of ABA is about 11 to 27 mg/l. Levels of gelling agents which are suitable for use in this method in the embryo development medium include the following: 6.0 to 12.0 g/l of agar, 1.75 to 4.00 g/l of gellan gum, 6.0 to 8.0 g/l of agarose, and 3.5 to 6.0 g/l of AGARGEL.

While the tissue mass may be cultured on the embryo development medium under lighted conditions, it is preferred to culture the tissue mass in a dark environment.

In certain cases it may be preferable to transfer the mass of embryogenic tissue from culture maintenance medium to embryo predevelopment medium for a period of 1 to 21 days prior to transferring the mass to embryo development medium. Embryo predevelopment medium suitable for use in the present method has an osmolality level in the range of 120 to 180 mM/kg and contains a sufficient amount of nutrients, from 1.0 to 10.0 g/l of activated carbon, and from 20.0 to 35.0 g/l of sugar selected from the group consisting of glucose, maltose, sucrose, and combinations thereof. Levels of gelling agents which are suitable for use in this method in the embryo predevelopment medium include the following: 6.0 to 9.0 g/l of agar, 1.75 to 3.50 g/l of gellan gum, 6.0 to 8.0 g/l of agarose, and 3.5 to 5.0 g/l of AGARGEL.

After the stage 3 somatic embryos have developed they are partially dried or dehydrated via exposure to an atmosphere having a high relative humidity (e.g., greater than 90% up to 99%) for sufficient time to permit the embryos to lose about 25% to 75% of their pre-dried weight (usually a period of about 2 to 5 weeks). The amount of moisture to be removed an embryo depends upon several factors, including the genotype of the embryo, the culture medium used, and the storage products contained in the embryo. It is well within the ability of a skilled artisan to determine the optimum moisture loss necessary to prepare each embryo for germination.

The partially dried somatic embryos are subsequently transferred to germination medium until germination occurs (usually about 1 to 8 weeks). These germinated embryos are converted into acclimatized somatic embryo plants via the manipulation of environmental factors prior to field planting.

In the present method it is further preferred to cover each of the above noted mediums (culture initiation medium, culture maintenance medium, embryo predevelopment medium, embryo development medium, and germination medium) with a sterile permeable membrane. The respective embryogenic cultures are subsequently placed upon the membrane instead of being placed directly upon the medium. The permeablity of the membrane allows the free-flow of materials between the culture and the medium. This modification greatly facilitates subsequent transfer of embryogenic cultures by avoiding direct contact with and disturbance of the cultures during transfer (see Example 8 below).

A number of terms are known to have differing meanings when used in the literature. The following definitions are believed to be the ones most generally used in the field of botany and are consistent with the usage of the terms in the present specification.

A "cell line" is a culture that arises from an individual explant.

"Corrosion cavity" is the cavity within the megagametophyte tissue of conifers formed by the growth and enlargement of the zygotic embryos.

"Conversion" refers to the acclimatization process that in vitro derived germinating somatic embryos undergo in order to survive under ex vitro (nonaxenic) conditions, and subsequent continued growth under ex vitro conditions.

"Cyropreservation" refers to the common process of storing cultures at ultra-low temperatures for future use.

A "dominant zygotic embryo" is one zygotic embryo among the multiple embryos formed in conifer seeds due to simple and cleavage polyembryony that outgrows the other zygotic embryos and matures in the seed.

An "embryogenic culture" is a plant cell or tissue culture capable of forming somatic embryos and regenerating plants via somatic embryogenesis.

"Embryogenic tissue" in conifers, is a mass of tissue and cells comprised of very early stage somatic embryos and suspensor-like cells embedded in a mucilaginous matrix. The level of differentiation may vary significantly among embryogenic conifer cultures. In some cases, rather than containing well formed somatic embryos, the embryogenic tissue may contain small, dense clusters of cells capable of forming somatic embryos.

"Epicotyl" is the first newly formed shoot to develop and grow after the seed leaves (cotyledons).

An "explant" is the organ, tissue, or cells derived from a plant and cultured in vitro for the purpose of starting a plant cell or tissue culture.

"Extrusion" is the process by which zygotic embryos and/or embryogenic tissue derived from zygotic embryos emerges or extrudes from the corrosion cavity of the megagametophyte of conifer seeds via the opening in the micropylar end, when placed in culture.

"Field planting" is the establishment of laboratory, greenhouse, nursery, or similarly grown planting stock under field conditions.

"Genotype" is the genetic constitution of an organism; the sum total of the genetic information contained in the chromosomes of an organism.

"Germination" is the emergence of the radicle or root from the embryo.

"Initiation" is the initial cellular proliferation or morphogenic development that eventually results in the establishment of a culture from an explant.

"Megagametophyte" is haploid nutritive tissue of the conifer seed, of maternal origin, within which the conifer zygotic embryos develop.

"Micropyle" is the small opening in the end of the conifer seed where the pollen tube enters the ovule during fertilization, and where embryogenic tissue extrudes from the megagametophyte during culture initiation.

"Nutrients" are the inorganics (e.g., nitrogen), vitamins, organic supplements, and carbon sources necessary for the nourishment of the culture.

A "plantlet" is a small germinating plant derived from a somatic embryo.

"Regeneration", in plant tissue culture, is a morphogenic response to a stimuli that results in the production of organs, embryos, or whole plants.

"Stage 1 embryos" are small embryos consisting of an embryonic region of small, densely cytoplasmic cells subtended by a suspensor comprised of long and highly vacuolated cells.

"Stage 2 embryos" are embryos with a prominent (bullet shaped) embryonic region that is more opaque and with a more smooth and glossy surface than stage 1 embryos.

"Stage 3 embryos" are embryos with an elongated embryonic region with small cotyledons visible.

"Somatic embryogenesis" is the process of initiation and development of embryos in vitro from somatic cells and tissues.

A "somatic embryo" is an embryo formed in vitro from vegetative (somatic) cells by mitotic division of cells. Early stage somatic embryos are morphologically similar to immature zygotic embryos; a region of small embryonal cells subtended by elongated suspensor cells. The embryonal cells develop into the mature somatic embryo.

A "suspensor cell" is an extension of the base of the embryo that physically pushes the embryo into the megagametophyte in conifer seeds and is comprised of elongated and highly vacuolated cells.

A "zygotic embryo" is an embryo(s) which is derived from the sexual fusion of gametic cells.

The following examples are provided to further illustrate the present invention and are not to be construed as limiting the invention in any manner.

EXAMPLE 1

The following multi-step method, when used in combination sequentially, has proven effective for regeneration of loblolly pine (*Pinus taeda L.*) by somatic embryogenesis. The procedure is as follows:

Step 1: Explant Collection And Preparation For Culture

Immature seed cones were collected from several different loblolly pine (*Pinus taeda L.*) sources located in Westvaco's South Carolina coastal breeding orchards near Charleston, South Carolina. The seed cones were collected when the dominant zygotic embryo was at the precotyledonary stage of development. Using the classification system of Hakman and von Arnold (1988), the dominant zygotic embryo at this stage is referred to as being at stage 2; that is, an embryo with a prominent embryonic region with a smooth and glossy surface, subtended by elongated suspensor cells which are highly vacuolated. Embryos which have progressed further in their development (to stage 3) will have cotyledon primordia, and will not be at an optimum stage of development for culture initiation. Although zygotic embryos at an earlier stage of development (stage 1) were also used effectively to initiate embryogenic cultures, Stage 2 embryos were optimum (and therefore preferred). The stage of zygotic embryo development was checked by extracting megagametophytes from seeds, longitudinally dissecting megagametophytes, and removing zygotic embryos for examination. This extraction and examination of the zygotic embryos was done under a dissection microscope. Loblolly pine cones collected from breeding orchards in the Charleston, South Carolina area reach the desired precotyledonary stage of development (stage 2) in mid to late July. Based on the finding that fertilization in loblolly pine occurred in mid June, the optimum stage corresponded to about 4 to 6 weeks post-fertilization.

Seed cones were harvested from selected trees, placed in plastic bags and stored at 4° C. until used for culture initiation. If the cones were stored for more than two weeks at 4° C., they were aired and dried out weekly (placed at 23° C., ambient laboratory conditions for 2-3 hours) to prevent growth of fungi on the surface of the cones and concomitant deterioration of seed quality.

For culture initiation intact seeds removed from seed cones were surface sterilized by treatment in a 10 to 20% commercial bleach solution (equivalent of a 0.525% to 1.050% sodium hypochlorite solution) for 15 minutes followed by three sterile water rinses (each of five minutes duration). Seeds were continuously stirred during the sterilization and rinsing process.

Step 2: Culture Initiation

Steps 2-4 were performed in a laminar-flow hood, routinely used to perform aseptic plant tissue culture techniques. Megagametophytes containing developing zygotic embryos were used as the explant for culture initiation. The seed coats of individual seeds were cracked open with the use of a sterile hemostat. The intact megagametophyte (which contains the developing zygotic embryos) was removed from the opened seed coat with forceps. Tissues attached to the megagametophyte, such as the megagametophyte membrane and the nucellus were removed from the megagametophyte and discarded. The megagametophte was placed on culture medium (longitudinal axis of megagametophyte parallel to the surface of culture medium) with forceps. The micropyle end of the megagametophyte was placed in contact with (but not submerged in) the culture medium.

Basal salt mixtures which have proven effective for culture initiation include the DCR basal salts formulation listed in Table I. (The complete formulations of the DCR medium used in the Examples are listed in Table II.). The pH of the medium was adjusted to 5.8 with KOH and HCl prior to autoclaving at 110 kPa (16 psi) and 121° C. for 20 minutes. Aqueous stock solutions of L-glutamine were filter sterilized and added to warm (about 60° C.) medium prior to pouring the medium into culture plates. Approximately 20 ml of medium was poured into 100×15 mm sterile plastic petri plates.

After megagametophyte explants were placed in culture, the perimeter of the plate was sealed with two wraps of PARAFILM ® (manufactured by American Can Co.). The plates were incubated in the dark at a constant temperature of 23° C. After about 7 to 21 days, embryogenic tissue extruded from the micropyle of the megagametophyte explants. After 28 days in culture embryogenic tissue was removed from responsive megagametophyte explants and moved to a new position on the same culture plate, or the embryogenic tissue was transferred to a new culture plate containing the same culture medium as used for initiation. Each individual culture derived from an individual megagametophyte explant was kept separate and assigned a cell line identification code.

Over 2000 explants were tested in nine different experiments to illustrate the effect of different levels of gelling agents on initiation of pine embryogenic tissue. Two culture media were employed in these experiments: $DCR_1$ (Table II) and $SH_1$ (SH inorganic salts; Schenk and Hilderbrandt (1972) with other components as in $DCR_1$). The pooled results from all nine experiments show that more embryogenic cultures were initiated on the low level of gelling agents than on normal or high levels (see Table IV below). The initiation results are given as both the frequency of embryogenic tissue extrusion from the explant and also embryogenic tissue proliferation. The frequency of extrusion provides a measure of how many explants showed potential for culture initiation, whereas the proliferation measures the number which produced vigorously growing embryogenic tissue.

TABLE IV

Summary of Overall Results Of 9 Experiments Conducted To Test Effect On Initiation of Pine Embryogenic Tissue (ET) Using Different Gelling Agent Levels.

| Gelling Agent Level | Frequency (%) explants | |
|---|---|---|
| | Extrude ET | Proliferate ET |
| Low | 305/672 (45) | 112/672 (17) |
| Normal | 258/672 (38) | 82/672 (12) |
| High | 236/672 (35) | 72/672 (11) |

The levels of gelling agents tested are classified as low, normal, and high as follows: The low level of gelling agents (1 g/l of GELRITE, 4 g/l of agar, 2 g/l of AGARGEL, and 4 g/l of low gelling temperature agarose) are lower than levels traditionally taught for plant tissue culture usage. The normal levels (2 g/l of GELRITE, 8 g/l of agar, 4 g/l of AGARGEL, and 6 g/l of LGT agarose) are levels commonly taught for plant tissue culture usage. The high levels (4 g/l of GELRITE, 12 g/l agar, 6 g/l of AGARGEL, and 8 g/l of LGT agarose) are generally considered to be higher than typically used in plant tissue culture.

A more detailed summary of each of the nine experiments referenced in Table IV is provided by Table V below.

TABLE V

Summary Of 9 Experiments With Lower Levels Of Gelling Than Commonly Used To Initiate Pine Embryogenic Tissue (ET).

| Expt No. | Seed source | Culture medium | Gelling agent[b] | Number[a] (%) explants Extrude ET at 4 weeks | Proliferate ET at 10 weeks |
|---|---|---|---|---|---|
| 1 | A45 × A26 | DCR$_1$ | GELRITE | 39 (81%) | 5 (10%) |
|   |           |         | Agar    | 35 (73%) | 12 (25%) |
| 2 | A10       | DCR$_1$ | GELRITE | 31 (65%) | 2 (4%) |
|   |           |         | Agar    | 26 (54%) | 4 (8%) |
| 3 | B19[c]    | DCR$_1$ | GELRITE | 22 (46%) | 13 (27%) |
|   |           |         | Agar    | 14 (29%) | 7 (15%) |
| 4 | A38 × A45 | DCR     | GELRITE | 7 (15%)  | 4 (8%) |
|   |           |         | Agar    | 9 (19%)  | 4 (8%) |
| 5 | A10 × A45 | DCR$_1$ SH$_1$ | GELRITE AGARGEL[d] | 17 (35%) 11 (23%) | 4 (8%) 4 (8%) |
| 6 | A38 × A45 | SH$_1$  | GELRITE | 12 (25%) | 4 (8%) |
| 7 | A19       | SH$_1$  | GELRITE | 37 (77%) | 27 (56%) |
| 8 | A10 × A45 | SH$_1$  | GELRITE | 10 (21%) | 1 (2%) |
| 9 | A45 × A33/38 | SH$_1$ | LGT[e] Agarose | 35 (73%) | 21 (44%) |
|   |           | DCR$_1$ totals: |    | 200 (46%) | 55 (13%) |
|   |           | SH$_1$ totals:  |    | 105 (44%) | 57 (24%) |
|   |           | Overall totals: |    | 305 (41%) | 112 (17%) |

[a]The number of responsive explants per gelling agent are listed. Forty-eight explants were cultured on each gelling agent in each experiment.
[b]Media gelled with agar contained TC agar (#19-8202, manufactured by Carolina Biol. Supply Co.).
[c]B19 was an interspecies hybrid (*Pinus rigida* × *Pinus taeda*) seed source.
[d]AGARGEL (#A3301, purchased from Sigma Chem. Co.).
[e]LGT (low gelling temperature) agarose (#A6560, purchased from Sigma Chem. Co.).

We purposely conducted these experiments with explants derived from genetically different seed sources (including both responsive seed sources and recalcitrant seed sources) in order to determine the effects of low levels of gelling agents on a broad range of genetic material. The results in Table V suggest that there was an interactive effect between the seed source and the type of gelling agent used. For example, in experiments 1 and 2, with seed sources A45×A26 and A10, agar resulted in about double the proliferation frequency than GELRITE. Whereas, in experiment 3, with seed source B19, the opposite was found, and explants on GELRITE proliferated more embryogenic tissue than on agar. Thus, one particular gelling agent type may not be optimum for use across all seed sources.

In addition, we purposely conducted several experiments listed in Table V (numbers 5–9) on SH$_1$ medium to verify that the positive effect of using low gelling agents was not restricted to the DCR$_1$ culture medium. As indicated previously, proliferation frequencies of 1 to 5% have typically been reported for Pinus species conifers. It is clear, therefore, from the results shown in Table V that high extrusion and proliferation were obtained on both DCR and SH$_1$ medium with several seed sources by using lower than conventional levels of gelling agents.

The data presented above on the effect of gelling agent levels on extrusion and proliferation of embryogenic tissue measured the frequencies of culture initiations. Additionally, in eight of the nine experiments we also measured culture weight in relation to gelling agent level. The results showed that not only were more cultures initiated on media containing low gelling agent levels, but that the cultures thus initiated were more vigorous and weighed more than cultures initiated on media containing normal or high levels of gelling agent.

Figure 2:
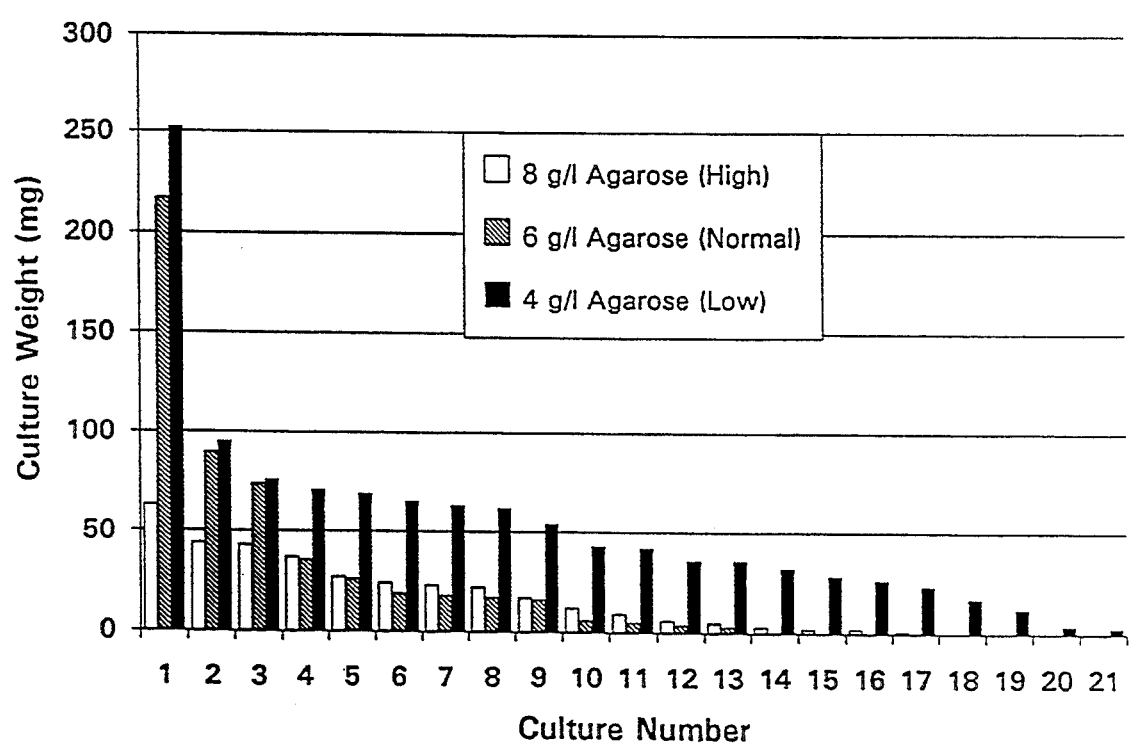
FIG. 2 shows the effect of gelling agent concentrations on culture initiations for seed source A45-×A33/38.

FIGS. 1 and 2 in the drawing further illustrate these findings. The responsive cultures are ranked from left to right according to culture weight.

Thus, not only did more explants produce vigorous embryogenic tissue, but the weight of embryogenic tissue produced was highest using a low level of gelling agent. For example, on the low level of GELRITE a total of 13 cultures proliferated a cumulative total of 1102 milligrams (mgs) of embryogenic tissue from seed source B19, whereas on the conventional level of GELRITE 6 cultures proliferated a cumulative total of 124 mgs of embryogenic tissue (FIG. 1). It is important to obtain rapid growth early in the culture establishment process in order to quickly multiply the embryogenic tissue for subsequent use. Our results suggest that using lower levels of gelling agents than is commonly used in conifer tissue culture improves the frequency of rapidly proliferating pine embryogenic cultures.

This is a significant finding for initiation of embryogenic tissue in Pinus species, because unlike Picea species, most workers find Pinus initiation to be extremely difficult. Any improvement in the initiation process which results in more embryogenic cultures being established translates into more embryogenic cultures being available for use in the regeneration process. Having a higher initiation frequency is critical since it increases the probablility of being able to identify superior culture genotypes for use in large scale production of clonal planting stock. In the past the limited number of embryogenic cultures available for regeneration has been a major limitation for implementation of somatic embryogenesis in Pinus species. Thus, all three parameters measured—(1) extrusion frequency, (2) proliferation frequency, and (3) growth as measured by the total weight of embryogenic tissue—were improved by using low levels of gelling agents.

Step 3: Culture Maintenance

Cultures were maintained on semi-solid medium, i.e., DCR$_1$ (Table II, the same medium as described for culture initiation) by subculturing masses of embryogenic tissue every 14 to 21 days to fresh medium. Culture maintenance conditions were the same as for culture initiation, except that the gelling agent levels contained in the culture maintenance media were increased. (It should be noted that the cultures could also be maintained as liquid suspension cultures on the same medium devoid of the gelling agent.)

Step 4: Embryo Development

At the end of a two to three week period on DCR medium, masses of embryogenic tissue (about 200 mg each) were either transferred to a MSG$_1$ predevelopment medium or to a MSG$_2$ development medium (see Table II above). The MSG$_1$ medium contained activated carbon. If the embryogenic tissue was placed on a MSG predevelopment medium, after about one week it was transferred to a MSG$_2$ development medium. As noted in Table II, the MSG$_2$ medium contained maltose, a carbon source (Uddin 1993), and ABA, but did not contain activated carbon.

All cultures were incubated at 23° C. in the dark. It is preferred that the cultures be incubated in the dark rather than light conditions, especially during the MSG$_2$ phase of embryo development out every 21 days the embryogenic tissue was transferred to fresh embryo development MSG$_2$ medium. After two passages on the MSG$_2$ medium, cotyledonary somatic embryos (stage 3) were visible on the surface of the embryogenic tissue. Typically, multiple harvests of cotyledonary somatic embryos were made at the end of the second and third passage, and sometimes after the fourth passages on MSG$_2$ medium. Subsequently the embryogenic tissue became necrotic and produced very few, if any, cotyledonary somatic embryos on MSG$_2$ medium and the embryogenic tissue was discarded. (It should be noted that the original culture from which the embryogenic tissue had been derived was concurrently maintained as a stock culture on DCR medium as described in step 2.)

The effect of the ABA level contained in the development medium on production of harvestable stage 3 somatic embryos (SEs) of *Pinus taeda* from an individual embryogenic culture genotype initiated from seed source A4 was evaluated. Three pieces of embryogenic tissue of about 200 mg each were tested on each ABA level, and the results are listed in Table VI below.

TABLE VI

Effect Of Abscisic Acid Levels On Somatic Embryos

| ABA level (mg/l) | Number of stage 3 SEs harvested |
|---|---|
| 0 | 9 |
| 11 | 133 |
| 22 | 157 |
| 33 | 114 |

The results show that very few harvestable stage 3 somatic embryos were produced when no ABA was employed in the embryo development medium.

The effect of abscisic acid concentration in the embryo development medium was further evaluated utilizing cultures from different seed sources and following the method taught in Steps 1–4 above. The results are shown in Table VII below.

TABLE VII

Effect Of Abscisic Acid Levels On Somatic Embryos From Different Seed Sources

| Culture code | Seed source | ABA concentration (mg/l) | | | | |
|---|---|---|---|---|---|---|
| | | 5 | 11 | 16 | 21 | 27 |
| 1 | A6 | 6 | 37 | 54 | 98 | 7 |
| 2 | A44 | 0 | 10 | 10 | 21 | 72 |
| 3 | A26 | 0 | 4 | 39 | 23 | 22 |

As noted above, in the present method it is preferred to incorporate ABA into the embryo development media in an amount ranging from 5 to 33 mg/l. The more preferred range of ABA is about 11 to 27 mg/l.

Step 5: Embryo Maturation Drying

Pine somatic embryos were prepared for germination by a maturation drying treatment which reduced their water content by an average of about 50%. This technique, referred to as "partial drying" (Kermode et al. 1989) was first used to improve germination of immature caster bean seeds (Kermode and Bewley 1985). The authors hypothesized that partial drying terminated the embryo development process and initiated metabolic processes necessary to prepare the embryo for germination and subsequent growth. Roberts (1993) used a similiar treatment to improve germination of Picea somatic embryos.

Stage 3 somatic embryos were transferred with forceps to the bottom surface of six empty wells of a 12-well plastic plate. The remaining six wells had previously been half-filled with sterile water. Typically, not more than 20 somatic embryos were placed in each empty well. The perimeter of the plate was sealed with two wraps of PARAFILM and incubated for approximately 21 days in the dark at 23° C. Our measurements showed that the Pinus somatic embryos lost between 35 to 64% of their original fresh weight during the partial drying treatment.

Step 6: Germination

Partially dried somatic embryos were placed horizontally on the surface of MSG]medium. The medium was in 100×15 mm sterile plastic petri plates. Typically, about 16 to 25 somatic embryos were placed in each plate. The perimeter of plates were wrapped twice with PARAFILM. Plates with embryos were incubated in the dark at 23° C. until the embryos elongated to approximately 1 to 2 cm (usually about 10 to 14 days). At this time the germination process had begun, with the emergence of the radicle (root) on some somatic embryos. Plates with the germinating somatic embryos were then transferred to a 16-hour fluorescent light and 8-hour dark photoperiod at 25° C.

A total of 6585 somatic embryos from 123 different culture genotypes were tested for germination via the above 30 procedure. Of these, 2657 (40%) germinated from 101 (82%) different genotypes. Forty-six genotypes (38%) of somatic embryos had germination frequencies of at least 50%. Six genotypes had germination levels above 75%.

Step 7: Conversion

The term "conversion" includes the acclimatization process that in vitro derived germinating somatic embryos undergo in order to survive under ex vitro (nonaxenic) conditions, and subsequent continued growth under ex vitro conditions.

When the length of the roots reached about 2 to 3 cm the germinating plantlets were aseptically removed from the plates and placed on moistened filter paper in a 100×15 mm petri plate. Although plantlets may later be placed in sterilized potting mix, they were no longer maintained in an axenic environment from this time on. Plants were then transplanted into either: (1) sterilized GRACE FORESTRY MIX (a soil mixture manufactured by T. R. Grace & Co.) in MAGENTA BOXES (containers manufactured by Magenta Corp.); or (2) TECHNICULTURE PEAT PLUGS (peat plugs manufactured by Techniculture Inc.). The boxes containing plantlets were sealed with PARAFILM and placed in a growth chamber with a 16-hour fluorescent and incandescent light and an 8-hour dark photoperiod at 23° C. The plantlets in peat plugs were enclosed in a plastic container used for growing seedlings and sealed with clear plastic cover to maintain a high relative humidity. The container was placed in a growth chamber under the same conditions as the boxes. Plantlets were fertilized weekly with a nutrient solution containing 50 ppm inorganic nitrogen and watered with reverse osmosis treated water as needed in order to keep potting mix or peat plugs from drying out.

When the plantlets formed epicotyls (newly formed shoots approximately 2 to 4 cm), they were transferred to leach tubes (RAY LEACH "CONE-TAINERS" ® #SSCUV manufactured by Stuewe & Sons, Inc.). Plantlets in boxes were transplanted into leach tubes containing a potting mix (2:1:2 peat:perlite:vermiculite, containing 602 g/m$^3$ OSMOCOTE ® fertilizer (18-6-12), 340 g/m$^3$ dolomitic lime and 78 g/mMICRO-MAX ® micronutrient mixture (manufactured by Sierra Chem. Co.). Plantlets in peat plugs were inserted directly (peat plug with intact plantlet) into potting mix contained in leach tubes. The leach tubes were placed in a greenhouse mist chamber. The environmental conditions in the mist chamber are as follows:

(1) Mist was applied for 30 seconds every 30 minutes from 6:00 a.m. to 6:30 p.m., and for 30 seconds every 60 minutes from 6:30 p.m. to 6:00 a.m.;
(2) Temperature was maintained at 26 to 31° C. during the day and at 18 to 20° C. at night; and
(3) Ambient light was admitted through black polypropylene shade cloth (51% shade) covering the greenhouse. Supplemental light from high pressure sodium bulbs was provided to produce a total photoperiod of about 16 hours.

When the plantlets had grown to approximately 8 to 16 cm in height, trays containing the resulting somatic embryo plants in leach tubes were removed from the mist chamber and placed on an open bench in the greenhouse for at least two weeks for acclimatization. Subsequently, somatic embryo plants in leach tube trays were moved to a shadehouse (framed structure covered with black polypropylene shade cloth) for approximately two weeks, and then to ambient outdoor conditions for an additional two weeks. Somatic embryo plants in leach tubes were watered with reverse osmosis treated water as required both during the greenhouse, shadehouse, and outdoors acclimatization period.

Following the above procedure, a total of 1567 germinated somatic embryos from 91 different culture genotypes were tested for conversion to vigorously growing somatic embryo plants. Of these germinants a total of 328 were converted to vigorously growing somatic embryo plants; a 21% conversion frequency.

Step 8: Field Planting

Acclimatized somatic embryo plants were carefully removed from the leach tubes so that the potting mix remained attached to roots and transplanted to a prepared field site. The field plantings were done on two consecutive years (1991 and 1992). In the 1991 field planting, 51 somatic embryo plants from six different genotypes were planted in the field. The number of plants per genotype ranged from 1 to 22. In the 1992 field planting, 292 somatic embryo derived plants from 61 genotypes were planted in the field. The number of plants per genotype ranged from 1 to 28. To date, 335 of the 343 somatic embryo plants (98%) have survived and appear phenotypically normal relative to standard *Pinus taeda* seedlings planted at the same times.

SUMMARY OF RESULTS

The present method results in significant improvements both in the number genotypes responsive to somatic embryogenesis and in the number of plants regenerated from the cultures. While others working in the field of somatic embryogenesis have attempted to provide protocols for Pinus species, the present method (here demonstrated employing *Pinus taeda*) has proven to be extremely effective on a broad range of diverse genetic material, thereby resulting in the production of large numbers of somatic embryos from numerous genotypes. This had not been possible with any Pinus species prior to this invention. One should note the importance of the sequential application of steps 1 through 7, which enabled successful completion of the entire regeneration process and establishment of *Pinus taeda* somatic embryo plants in field plantings.

EXAMPLE 2

*Pinus rigida* is native to eastern North America (New Brunswick) to southeastern U.S. (Georgia) and is classified as an Eastern hard pine (Peterson 1989). *Pinus taeda*, a southern yellow pine with native distribution which extends as far north as New Jersey, is more productive in the southeastern U.S. and gulf states. Interspecies hybrids between *Pinus rigida* and *Pinus taeda* are of commercial interest because the hybrid retains desirable characteristics of each species; namely, the increased cold hardiness of *Pinus rigida* and some of the superior growth potential of *Pinus taeda*. Breeding efforts have resulted in desirable parental selections of *Pinus rigida* and *Pinus taeda* which yield $F_1$ hybrid seed for production of planting stock for reforestation in regions that extend north of where *Pinus taeda* is productive. Currently production of interspecies $F_1$ hybrid seed is achieved through supplemental mass pollination of *Pinus rigida* with *Pinus taeda* pollen. But, it is frequently difficult to produce large quantities of $F_1$ hybrid seed due to embryo abortion resulting in poor seed production. Production of $F_1$ hybrid clonal planting stock by somatic embryogenesis, therefore, offers a potential alternative for efficient large scale production from selected superior genotypes of interspecies Pinus hybrids.

To date, the only report of somatic embryogenesis and plant regeneration from interspecies conifer hybrids was with Larix×Eurolepis (Klimaszewska 1989). There has been no progress, to our knowledge, on development of a somatic embryogenesis protocol completing the entire plant regeneration process that has proven effective for Pinus interspecies hybrids. The present invention solves this problem and provides a somatic embryo regeneration system for the interspecies hybrid of *Pinus rigida*×*Pinus taeda* that has demonstrated success with established field plantings of $F_1$ hybrid clonal planting stock.

We have found the method described in the Example 1 to be effective on initiating embryogenic cultures and regenerating $F_1$ hybrid somatic embryo plants of *Pinus rigida*×*Pinus taeda*. To illustrate this we followed Steps 1–3 of the method taught in Example 1 in order to evaluate ten genetically diverse *Pinus rigida*×*Pinus taeda* seed sources (labeled B1–B10) for the proliferation of embryogenic tissue from immature seeds. The results are listed in Table VIII below.

TABLE VIII

| Proliferation of Embryogenic Tissue from Ten *Pinus rislida* × *Pinus taeda* Seed Sources | | |
|---|---|---|
| Seed source | No. seeds cultured | Percent proliferation |
| B1[b] | 55 | 7 |
| B2[a] | 29 | 14 |

TABLE VIII-continued

Proliferation of Embryogenic Tissue from Ten
*Pinus rislida* × *Pinus taeda* Seed Sources

| Seed source | No. seeds cultured | Percent proliferation |
|---|---|---|
| B3[a] | 83 | 11 |
| B4[a] | 95 | 9 |
| B5[a] | 96 | 13 |
| B6[a] | 25 | 8 |
| B7[a] | 40 | 5 |
| B8[a] | 48 | 6 |
| B9[c] | 145 | 19 |
| B10[c] | 145 | 6 |

[a] *Pinus rigida* maternal tree supplementally mass pollinated with *Pinus taeda* pollen.
[b] *Pinus rigida* × *Pinus taeda* F₁ hybrid maternal tree supplementally mass pollinated with *Pinus taeda* pollen.
[c] *Pinus rigids* maternal tree control pollinated with *Pinus taeda* pollen.

As previous reports of Pinus species have typically obtained proliferation rates of only 1 to 5%, it is clear from the data shown in Table VIII that excellent proliferation results were achieved using the present method.

Somatic embryos were developed from 24 $F_1$ hybrid culture genotypes from 12 genetically different *Pinus. rigida* × *Pinus taeda* parental combinations via the procedure taught in Steps 1-4 of Example 1. Twenty-one of the 24 $F_1$ hybrid culture genotypes (88%) were responsive and produced harvestable cotyledonary somatic embryos. Twenty-five percent of the responsive genotypes produced more than 100 harvestable somatic embryos per genotype. A total of 1706 cotyledonary somatic embryos were harvested from 10 of the 12 seed sources tested.

Several evaluations conducted with $F_1$ hybrid embryogenic culture genotypes have demonstrated the potential for producing large numbers of *Pinus rigida* × *Pinus taeda* $F_1$ hybrid somatic embryos via the current invention method. Yields of harvestable stage 3 somatic embryos as high as 400 to 500 per gram of embryogenic tissue have been obtained. In one evaluation utilizing a $F_1$ hybrid culture genotype 4126 harvestable stage 3 somatic embryos were obtained from a total of 23 grams of embryogenic tissue. This is an average yield per gram of embryogenic tissue of 180 harvestable stage 3 somatic embryos.

Germination of $F_1$ hybrid somatic embryos of *Pinus rigida* × *Pinus taeda* obtained by following Steps 1-5 of Example 1 were achieved using Step 6 of Example 1. A total of 3705 somatic embryos from 23 different $F_1$ hybrid culture genotypes were tested, and 1116 (30%) germinated. Germinanting plantlets were obtained from 18 (78%) of the 23 genotypes tested. Germination frequencies were as high as 85% for ,one culture genotype (139 of 164 somatic embryos).

Conversion of germinated $F_1$ hybrid somatic embryos of *Pinus rigida* × *Pinus taeda* obtained utilizing Steps 1-6 of Example 1 were achieved by employing Step 7 of Example 1. A total of 399 germinated $F_1$ hybrid somatic embryos from 17 different culture genotypes were tested for conversion to vigorously growing plants. Of the 399 germinated embryos, a total of 173 were converted to vigorously growing plants; a 43% conversion frequency.

Field plantings of $F_1$ hybrid somatic embryo plants of *Pinus rigida* × *Pinus taeda* using Steps 1-7 of the Example 1 were achieved by employing Step 8 of Example 1. The field plantings were done on two consecutive years; 1991 and 1992. In 1991, 57 somatic embryo plants from two $F_1$ hybrid genotypes were field planted. In the 1992 field planting, 171 somatic embryo plants from 14 F hybrid genotypes were sown. The number of plants per genotype ranged from 1 to 129. To date, 202 of the 228 $F_1$ hybrid somatic embryo *Pinus rigida* × *Pinus taeda* plants (89%) have survived and appear phenotypically normal relative to conventional *Pinus rigida* × *Pinus taeda* $F_1$ hybrid seedlings.

EXAMPLE 3

The method taught in Example 1 was utilized in order to initiate embryogenic cultures and regenerate somatic embryo plants of *Pinus serotina* and *Pinus serotina* × *Pinus taeda*. *P. serotina* is a species native to the southeastern U.S., closely related to *Pinus taeda*, and of potential commercial value for reforestation on poorly drained field sites. Explants were derived from immature cones collected from two seed sources and tested for culture initiation. Proliferating embryogenic tissue was obtained from five different genotypes derived from two seed sources. Cotyledonary stage somatic embryos were obtained from one culture genotype of seed source C1. Four of 12 somatic embryos germinated. Two of the four germinated somatic embryos were established as vigorous plants under greenhouse conditions. The somatic embryo plants were similar in size and phenotypic appearance to the other Pinus somatic embryo plants produced in the first and second examples with *P. taeda* and *P. rigida* × *P. taeda*.

EXAMPLE 4

The following evaluation compared the present method with the process taught by Gupta and Pullman in U.S. Pat. No. 4,957,866—particularly the method of initiating the embryogenic culture as taught in Step 2 of Example 1 of the present method. Immature megagametophyte explants were tested from an open-pollinated seed source (A10) and a control-pollinated seed source (A45×A26). Previous experiments had consistently shown that explants derived from these two seed sources provide a range of capacity for somatic embryogenesis typically found in loblolly pine; from a recalcitrant seed source (A10) to a more responsive seed source (A45×A26). The culture initiation media compared were (1) $DCR_1$ (see Table II above), and
(2) $BM_1$ medium cited in Table 2 of U.S. Pat. No. 4,957,866. In brief, this is a modified ½P6 basal salts (Teasdale et al. 1986) with 2,4-D (11.1 mg/l), kinetin (4.3 mg/l) and BA (4.5 mg/l). After four weeks in culture the extruding embryogenic tissue from responsive explants was transferred to a maintenance medium as follows: (1) cultures on DCR were transferred to new plates of the same medium, (2) cultures on $BM_1$ were transferred to $BM_2$ medium cited in Table 2 of U.S. Pat. No. 4,957,866.

The results showed that both embryogenic tissue extrusion and proliferation frequency were improved by using the method of the current invention relative to the process taught in U.S. Pat. No. 4,957,866 (see Table X below). Very importantly, the present method resulted in the proliferation frequency of embryogenic tissue approximately doubled for both the responsive and the recalcitrant seed sources.

TABLE IX

Comparison of Embryogenic Tissue (ET) Initiation Frequencies of the Method Taught in the Current Invention (Step 1, Example 1) and the Process Taught in U.S. Pat. No. 4,957,866.

| Culture Initiation Medium | Frequency (%) explants | | | |
|---|---|---|---|---|
| | Extrude ET at 4 weeks | | Proliferate ET at 7 weeks | |
| | A10 | A45 × A26 | A10 | A45 × A26 |
| Present Method | 25/48 (52%) | 33/48 (69%) | 7/48 (15%) | 24/48 (50%) |
| U.S. Pat. No. 4,957,866 | 20/48 (42%) | 26/48 (54%) | 4/48 (8%) | 10/48 (21%) |

The most striking improvement was on the growth potential of the newly initiated embryogenic tissue. Not only did the method of the current invention result in more explants of both seed sources producing vigorous proliferation of embryogenic tissue, but the culture weight was improved by the method of the current invention relative to the process taught in U.S. Pat. No. 4,957,866.

Figure 3:
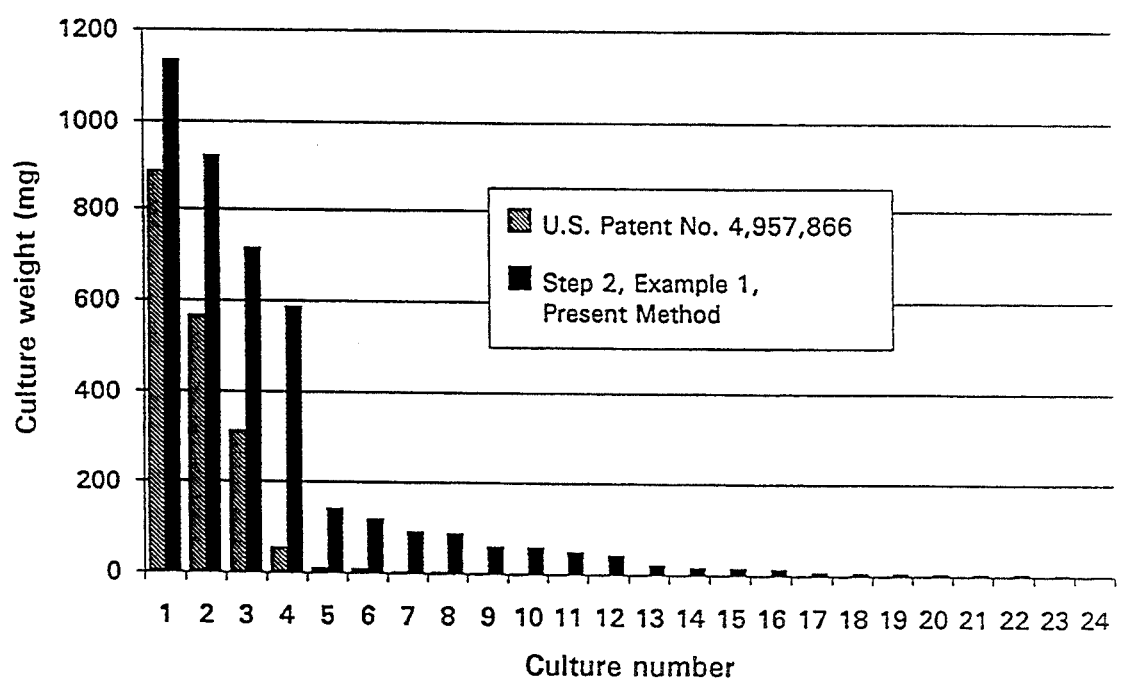
FIG. 3 shows the results achieved for seed source A45×A26.
Figure 4:
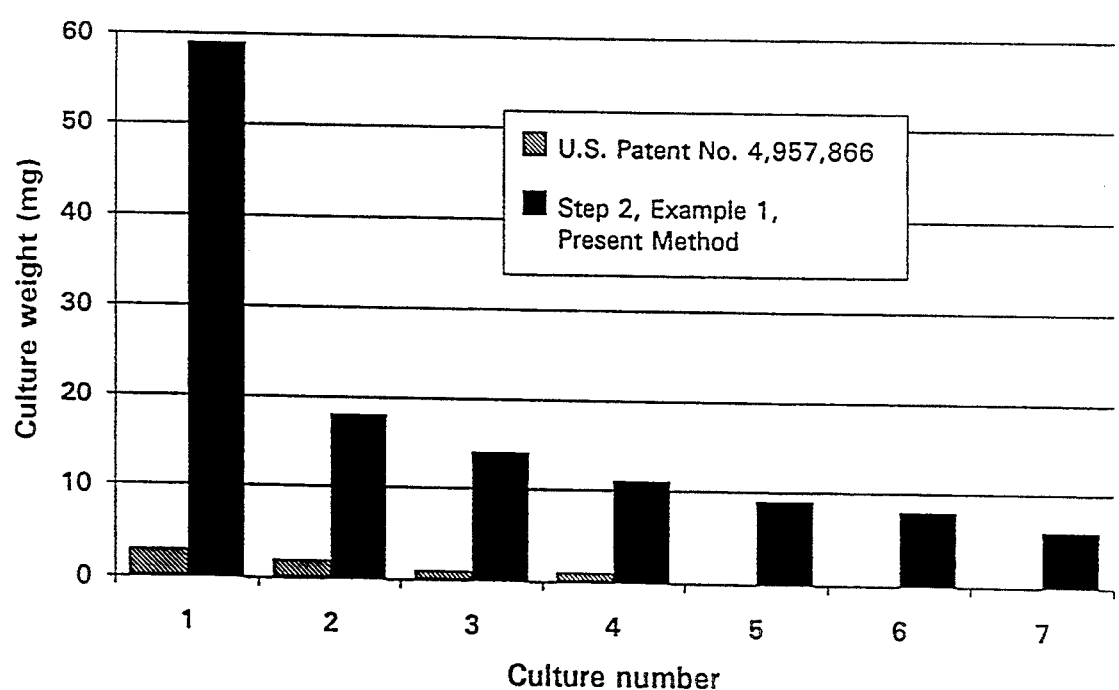
FIG. 4 shows the results achieved for seed source A10.

This improvement is graphically illustrated in FIGS. 3 and 4 in the drawings, which compares the total weight of each culture genotype produced via the different methods as measured after 10 weeks. Employment of the present method resulted in a total of cultures from seed source A45×A26 proliferating a cumulative total of 4.11 grams of embryogenic tissue. In contrast, use of the patented process resulted in only 10 cultures proliferating a cumulative total of 1.85 grams of embryogenic tissue (FIG. 3).

EXAMPLE 5

The following evaluation compared the present method with the process taught by Pullman and Gupta in U.S. Pat. No. 5,034,326—particularly the method of producing stage 3 somatic embryos from embryogenic cultures of *Pinus taeda* as taught in Step 4 of Example 1 of the present method. The embryogenic cultures used in this example were derived from the experiments described in Example 4. Two somatic embryo development methods were evaluated: First, according to the process taught in U.S. Pat. No. 5,034,326, the embryogenic cultures were initiated on $BM_1$ medium (see Example 4), maintained on $BM_2$ medium, subcultured onto $BM_3$ Late Proembryo Development Medium, and finally tested for production of stage 3 somatic embryos on $BM_4$ Embryo Development medium. After approximately 3 months on $BM_2$ medium only 3 of the 10 embryogenic cultures initiated from seed source A45×A26 on $BM_1$ employing the patented process survived (see FIG. 3, Example 4). The 3 surviving cultures were subcultured (every 3 weeks) to $BM_3$ Late Proembryo Development Medium for 9 weeks total time, and then transferred to $BM_4$ Embryo Development medium. In comparison, 12 of the 24 cultures initiated from seed source A45×A26 on $DCR_1$ (see FIG. 3, Example 4) survived after the same 3 month time in culture, were transferred to MSG predevelopment medium, and then to $MSG_2$ embryo development medium in accordance Step 4 of Example 1 of the present method. The results are summarized in Table XI below.

TABLE X

Comparison of Stage 3 Somatic Embryo Production of the Present Method (Step 4, Example 1) and the Process Taught in U.S. Pat. No. 5,034,326.

| Embryo Development Method | Total No. of Cultures Tested | Total No. of Pieces[a] of ET Tested | Total No of Stage 3 SEs harvested |
|---|---|---|---|
| Present Method | 12 | 59 | 238 |
| U.S. Pat. No. 5,034,326 | 3 | 12 | 0 |

It is clear from this evaluation that the method taught in the present invention was effective in producing large numbers of *Pinus taeda* stage 3 somatic embryos from numerous culture genotypes, whereas the process taught by U.S. Pat. No. 5,034,326 was ineffective. Only two of the 13 cultures tested using the present method did not produce any stage 3 somatic embryos, whereas all 3 cultures tested on the patented process produced zero harvestable stage 3 somatic embryos. While it is possible that stage 3 somatic embryos would be produced by the process taught by U.S. Pat. No. 5,034,326 if more cultures were screened, it is also evident from this evaluation that it would be extremely difficult to maintain cultures according to the process taught in U.S. Pat. No. 5,034,326, as only 3 of the original 10 cultures survived. It is also possible that the process taught in U.S. Pat. No. 5,034,326 might be more effective when employed with coniferous species other than Pinus (e.g., Pseudotsuga and Picea species).

EXAMPLE 6

The following evaluation compared the present method with the process taught by Gupta and Pullman in U.S. Pat. No. 4,957,866—particularly the method of obtaining somatic embryo development as taught in Step 4 of Example 1 of the present method. Embryogenic cultures of *Pinus taeda* and *Pinus rigida*×*Pinus taeda* used in this experiment were initiated and maintained according to method taught in Steps 1–3 of Example 1.

Three development protocols were tested, with Treatments A and B practicing the present method and Treatment C practicing the patented process. In Treatment A masses of embryogenic tissue were transferred from culture maintenance medium to $MSG_1$ embryo predevelopment medium for 7 days and then transferred to $MSG_2$ embryo development medium. In Treatment B masses of embryogenic tissue, which had been growing on $DCR_1$ maintenance medium, were transferred to the same DCR maintenance medium (containing 0.5 g/l inositol) for three 21 day subcultures, and then transferred to $MSG_2$ embryo development medium. In Treatment C masses of embryogenic tissue were transferred from culture maintenance medium to an embryo predevelopment medium ($DCR_1$ containing 10.0 g/l inositol) for three 21 day subcultures, and then transferred to $MSG_2$ embryo development medium.

In terms of osmolality differences the three embryo development protocols tested (Treatments A, B and C) differed as follows: Both Treatments A and B, according to the present method, utilized maintenance and predevelopment medium with (low) osmolality levels in the range of 145 to 165 mM/kg, and embryo development medium with (high) osmolality levels in the range of 250 to 260 mM/kg. Treatment C similarly utilized maintenance medium with osmolality levels in the (low) range of 145 to 155 mM/kg and embryo development medium with (high) osmolality levels in the range of 250 to 260 mM/kg. But Treatment C, in accordance with the patented process, differed from Treatments A and B by having a predevelopment medium with a (high) osmolality level of 230 mM/kg provided by the high level of inositol added to the medium. Thus, Treatment C tested the efficacy of using a predevelopment medium with significantly higher osmolality levels, in comparison to a either a predevelopment medium with low osmolality (Treatment A), or simply maintaining the cultures on a maintenance medium with low osmolality (Treatment B) for an equivalent period of time.

The results contained in Table XII below show that the present method (Treatments A or B) resulted in higher overall production of both stage 2 and stage 3 somatic embryos than the process taught in the patent of adding a high osmoticum predevelopment step (Treatment C). Only one culture genotype (#2) developed slightly more stage 3 somatic embryos by following the patented process (Treatment C). It should be noted that the only treatment that was effective in inducing production of stage 3 somatic embryos from culture genotypes maintained as liquid suspension cultures was Treatment A; which practiced the method taught in Example 1 of the present invention.

TABLE XI

Comparison of Precotyledonary (stage 2) and Cotyledonary (stage 3) Somatic Embryo Production on Three Different Development Protocols.

| Culture genotype no.[a] | Culture Origin[b] | Total no. (stage 2) and stage 3 somatic embryos produced on development protocol: | | |
|---|---|---|---|---|
| | | Trt. A | Trt. B | Trt. C |
| 1 | ET | (274) 178 | (346) 418 | (157) 134 |
| 2 | ET | (187) 29 | (273) 113 | (194) 118 |
| 3 | ET | (163) 89 | (69) 73 | (52) 44 |
| 4 | ES | (166) 36 | (57) 0 | (43) 0 |
| Totals: | | (790) 332 | (745) 604 | (446) 296 |

[a]Cell line 1 was Pinus rigida × Pinus taeda.
[b]Cell lines 2-4 were Pinus taeda.
ET (embryogenic tissue) cultures maintained on semi-solid media according to Step 3 of Example 1 prior to testing.
ES (embryogenic suspension) cultures maintained as liquid suspensions prior to testing.

The results in Table XI show that the method of the current invention is at least as effective, and for most culture genotypes tested far more effective, for producing stage 3 somatic embryos of Pinus taeda and Pinus rigida × Pinus taeda than the process taught by Gupta and Pullman (1990).

EXAMPLE 7

The current invention enables one to regenerate large numbers of Pinus taeda and Pinus rigida × Pinus taeda somatic embryos from embryogenic cultures which have been cryopreserved in liquid nitrogen. Cryopreservation is an essential component in developing an overall strategy for clonal propagation of Pinus species using somatic embryogenesis, Until now there has not been an efficient regeneration system available for Pinus species to use in conjunction with cryostorage procedures, Embryogenic cultures were cryopreserved in liquid nitrogen in order to:

(1) maintain a bank of cultures for retrieval and use after field tests have identified superior genotypes; and (2) insure against loss of culture genotypes due to contamination, loss of vigor associated with culture aging, or other deleterious changes that may occur during long-term culture maintenance.

The following method was very successfully used for cryopreservation of both Pinus taeda and Pinus rigida × Pinus taeda embryogenic cultures. Following the method taught in Steps 1-3 of Example 1 pieces of embryogenic tissue (7 to 14 days since their last subculture on the culture maintenance medium) were dispersed in liquid $DCR_1$ medium which contained 0.4 molar sorbitol (Klimazewska et al. 1992). Liquid embryogenic suspension cultures, produced via the method of Example 4, were also used as a source of tissue for cryopreservation. The amount of embryogenic tissue from either gelled or liquid medium used was sufficient to result in a 30% suspension (e.g., 3 ml volume of embryogenic tissue added to 7 ml of liquid medium). Erlenmeyer flasks containing the suspension were incubated for 24 hours in the dark on a gyratory shaker (100 rpm), and then placed on ice. Five aliquots of the cryoprotectant dimethylsulfoxide (DMSO) were added to the suspension to bring final concentration of DMSO to 10%. One milliliter aliquots of the cell suspension containing DMSO were then transferred to freezing vials (2 ml NALGENE Cryovials, Nalge Co.), placed in programmable freezer (Model 9000, Gordinier Electronics) and cooled to $-35°$ C. at $0.33°$ C. per minute. The freezing vials were then immersed in liquid nitrogen inside a cryobiological storage vessel (Model #CY50945, Thermolyne) for long-term storage.

For retrieval of frozen cultures, individual vials were removed from the cryobiological storage vessel and placed in 38° C. water to rapidly thaw the frozen cell suspension. The thawed cell suspension was aseptically poured from the cryovial onto a sterile NITEX nylon membrane (#3-35/16XX, Tetko, Inc.) which had been placed on top of two sterile filter papers (Whatman no. 2, Whatman International Ltd.) to absorb excess liquid from the cell suspension. The nylon membrane containing embryogenic tissue was then transferred to maintenance medium, e.g., $DCR_1$ and incubated at 23° C. for 24 hours to allow DMSO to diffuse into the medium. The nylon membrane containing embryogenic tissue was removed from the medium and transferred to a new plate of maintenance medium. Thereafter, the membrane containing embryogenic tissue was transferred to a new plate of maintenance medium every 21 days. When sufficient proliferation of the embryogenic tissue occurred, individual pieces (about 200 mg each) were transferred directly to maintenance medium for further multiplication or directly to embryo predevelopment medium according to a modification of Step 4 of Example 1. The modification was as follows: The masses of embryogenic tissue were transferred onto a sterile NITEX nylon membrane (No. 3-35/16XX, TETKO, Inc.) which had been placed on the surface of the predevelopment medium. This modification greatly facilitated subsequent transfer of the embryogenic tissue masses to embryo development medium, by avoiding direct contact with and disturbance of the masses during transfer. Instead, the nylon membrane containing the masses was easily transferred as a unit to embryo development medium, and also later easily transferred to new embryo development medium as described in Step 4 of Example 1.

Table XII summarizes somatic embryo yields from embryogenic cultures initiated according to Step 2 of Example 1 and cryopreserved as described above in comparison to yields from the same culture genotypes which had not been cryopreserved. Three of the four cultures tested produced more stage 3 somatic embryos after cryopreservation than before. These data show that the current invention, when used in combination with the above described cryopreservation method, enables one to effectively produce large numbers of both *Pinus taeda* and *Pinus rigida* × *Pinus taeda* somatic embryos from cryopreserved embryogenic cultures.

TABLE XII

Pine Somatic Embryos (SEs) Harvested from Cryopreserved (frozen to −196° C.) and Unfrozen Embryogenic Tissue (ET).

| Culture genotype | Parent Tree[a] | Cryo-preserved[b] | Total No. SEs harvested (No. pieces[c] ET) | No. SEs harvested per piece ET |
|---|---|---|---|---|
| 1 | B19 | yes | 518 (4) | 130 |
|   |     | no  | 347 (3) | 116 |
| 2 | B19 | yes | 384 (4) | 96 |
|   |     | no  | 474 (6) | 80 |
| 3 | A45 | yes | 194 (3) | 65 |
|   |     | no  | 180 (3) | 60 |
| 4 | A10 × A45 | yes | 362 (6) | 60 |
|   |     | no  | 261 (3) | 87 |

[a] B19 = *Pinus rigida* maternal tree supplementally mass pollinated with *Pinus taeda* pollen, A45 = open-pollinated *P. taeda*, and A10 × A45 = *P. taeda* maternal tree (A10) × *P. taeda* pollen (A45).
[b] Cryopreserved cultures were in liquid $N_2$ from 7 to 19 weeks.
[c] Each piece of ET approximately 200 mg fresh weight.

EXAMPLE 8

The following experiment was done to test modifications in the form of nitrogen and type of gelling agent used in the germination medium, $MSG_3$. The data summarized in Table XIII below used *Pinus taeda* embryogenic cultures initiated and maintained according to Steps 1–3 of Example 1 and somatic embryos developed and matured according to Steps 4 and 5 of Example 1. The somatic embryos were then germinated on either $MSG_3$ medium (according to Step 6 of Example 1) or MSN medium (which was equivalent to $MSG_3$ medium except the L-glutamine nitrogen was replaced with an equivalent molar concentration of inorganic nitrogen as ammonium nitrate, and GELRITE was replaced with agar). All other components of the two media were equivalent and as listed in Table II for $MSG_3$.

TABLE XIII

Effect of Medium Modifications on *Pinus taeda* Somatic Embryo Germination

| Germination Medium | Nitrogen[a] | Gelling agent | Culture genotype[b] | Germination (%)[c] |
|---|---|---|---|---|
| $KSG_3$ | L-glutamine 1.45 g/l | agar 8 g/l | 1 | 66 |
|   |   |   | 2 | 14 |
| MSN | $NH_4NO_3$ 0.8 g/l | GELRITE 2 g/l | 1 | 38 |
|   |   |   | 2 | 16 |

[a] In addition, each medium contained 0.1 g/l $KNO_3$.
[b] Somatic embryos from culture genotypes 1 and 2 derived from parent trees A38 × A45 and A45 × A33/38, respectively.
[c] Fifty somatic embryos of each culture genotype were tested for germination on each medium.

The results showed that germination of embryos from culture genotype 1 was highest on $MSG_3$ with L-glutamine and agar. Whereas, germination of embryos from culture genotype 2 was similar on either MSG medium with L-glutamine and agar, or on MSN medium with ammonium nitrate ($NH_4NO_3$) and GELRITE. The use of the MSN germination medium, with an inorganic form of nitrogen, is advantageous since the inorganic form of nitrogen is not heat labile and, therefore, does not require separate filter-sterilization as the L-glutamine does in $MSG_3$ medium. Therefore, an additional experiment (see Table XIV below) was done to study germination of *Pinus taeda* somatic embryos from a wide range of culture genotypes on MSN medium with ammonium nitrate and GELRITE.

EXAMPLE 9

The following experiment was done to verify that large numbers of *Pinus taeda* somatic embryo plants derived from a wide range of culture genotypes could be established as planting stock using: (1) the modified germination medium used in Example 9, MSN, which contained inorganic nitrogen and GELRITE; and (2) the conversion procedure used in Step 7 of Example 1. The data summarized in Table XIV below used *Pinus taeda* embryogenic cultures initiated and maintained according to Steps 1–3 of Example 1 and somatic embryos developed and matured according to Steps 4 and 5 of Example 1.

TABLE XIV

Germination and Conversion of Somatic Embryos (SEs) Derived from Three Control Crosses of *Pinus taeda*

| Parent Tree | Culture Genotype | No. SEs Tested | Germination No. (%) | Conversion No. (%)[a] |
|---|---|---|---|---|
| A45 × A10 | 1 | 144 | 104 (72) | 59 (57) |
|   | 2 | 129 | 38 (29) | 19 (50) |
|   | 3 | 85 | 35 (41) | 30 (86) |
|   | 4 | 110 | 74 (67) | 50 (68) |
|   | 5 | 60 | 22 (37) | 17 (77) |
|   | 6 | 61 | 16 (26) | 6 (38) |
| A38 × A45 | 7 | 73 | 41 (56) | 24 (59) |
|   | 8 | 98 | 23 (23) | 19 (83) |
|   | 9 | 130 | 21 (16) | 8 (38) |
|   | 10 | 63 | 5 (8) | 0 (0) |
|   | 11 | 162 | 146 (90) | 52 (36) |
|   | 12 | 74 | 37 (50) | 27 (73) |
| A10 × A45 | 13 | 263 | 72 (27) | 45 (63) |
|   | 14 | 75 | 15 (20) | 4 (27) |
|   | 15 | 132 | 54 (41) | 47 (87) |
|   | 16 | 140 | 76 (5%) | 46 (61) |
|   | 17 | 88 | 59 (67) | 43 (73) |
| Totals |   | 1887 | 838 (4%) | 496 (59) |

[a] Conversion calculated as the percentage of vigorous germinated somatic embryos which survived and continued to grow ex vitro.

The results in Table XIV showed that an overall germination frequency of 44% was obtained from 17 culture genotypes derived from three control pollinated trees. Thus, the MSN medium with inorganic nitrogen and GELRITE, was generally effective for germinating somatic embryos from numerous culture genotypes of *Pinus taeda*. Somatic embryos from only two of the 17 culture genotypes (numbers 9 and 10) of parent tree A38 × A45 had germination levels below 20%. In addition, the results in Table XIV showed that an overall conversion frequency of 59% was obtained with the methods of the current invention. Somatic embryos from only one culture genotype (number 10) did not produce vigorous planting stock. The results clearly demonstrated the potential of using the MSN germination medium and the conversion method in Step 7 of Example 1 to efficiently produce large numbers of *Pinus taeda* somatic embryo plants for field planting. The results presented in Table XIV are unprecedented for production of planting stock via somatic embryogenesis of the recalcitrant Pinus species conifers. It demonstrates the utility of the methods taught in this invention for solving the problem of providing a reproducible method for large scale production of *Pinus taeda* via somatic embryogenesis.

Many modifications and variations of the present invention will be apparent to one of ordinary skill in the art in light of the above teachings. It is therefore understood that the scope of the invention is not to be limited by the foregoing description, but rather is to be defined by the claims appended hereto.

BIBLIOGRAPHY

Becwar, M. R., S. R. Wann, M. A. Johnson, S. A. Verhagen, R. P. Feirer, and R. Nagmani. Development and Characterization of In Vitro Embryogenic Systems In Conifers. Somatic Cell Genetics of Woody Plants (p. 1-18) 1988.

Becwar, M. R., R. Nagmani, and S. R. Wann. Initiation of embryogenic cultures and somatic embryo development in loblolly pine (*Pinus taeda*). Canadian Journal of Forest Research 20:810-817, 1990.

Etienne, H., A. Berger, and M. P. Carron. Water status of callus from Hevea brasiliensis during induction of somatic embryogenesis. Physiologia Plantarum 82:213-218, 1991.

Finer, J. J., H. B. Kriebel, and M. R. Becwar. Initiation of embryogenic callus and suspension cultures of eastern white pine (*Pinus strobus L.*). Plant Cell Reports 8:203-206, 1989.

Grossnickle, S. C., D. R. Roberts, J. E. Major, R. S. Folk, F. B. Webster, and B.C. S. Sutton. Integration of somatic embryogenesis into operational forestry: Comparison of interior spruce emblings and seedlings during production of 1+0 stock. In: Proceedings, Intermountain Forest Nursery Association. Aug. 12-16, 1991. Park City, Utah. U.S.D.A. Forest Service, General Tech. Report RM-211. pp. 106-113, 1992.

Gupta, P. K. and D. J. Durzan. Shoot multiplication from mature trees of Douglas-fir (Pseudotsuga menziesii) and sugar pine (*Pinus lambertiana*). Plant Cell Reports 4:177-179, 1985.

Gupta, P. K. and D. J. Durzan. Somatic polyembryogenesis from callus of mature sugar pine embryos. Bio/Technology 4:643-645, July 1986.

Gupta, P. K. and D. J. Durzan. Biotechnology of somatic polyembryogenesis and plantlet regeneration in loblolly pine. Bio/Technology 5:147-151, February 1987.

Gupta, P. K. and G. S. Pullman. Method for reproducing coniferous plants by somatic embryogenesis. U.S. Pat. No. 4,957,866 issued Sep. 18, 1990.

Gupta, P. K. and G. S. Pullman. Method for reproducing coniferous plants by somatic embryogenesis using abscisic acid and osmotic potential variation. U.S. Pat. No. 5,036,007—issued Jul. 30, 1991.

Gupta, P. K., G. S. Pullman, R. Timmis, M. E. Kreitinger, W. C. Carlson, and D. E. Welty. Scale-up somatic embryogenesis of conifers for reforestation (Abstract). In: Proceedings, 3rd Inter. Assoc. of Plant Tissue Culture Canadian workshop on Plant Tissue Culture and Genetic Engineering, Univ. of Guelph, Guelph, Ontario, Canada. Jun. 17-20, 1992.

Hakman, I. and S. von Arnold. Plantlet regeneration through somatic embryogenesis in Picea abies (Norway spruce). Journal of Plant Physiology 121:149-158, 1985.

Hakman, I., L. C. Fowke, S. von Arnold, and T. Eriksson. The development of somatic embryos in tissue cultures initiated from immature embryos of Picea abies (Norway spruce). Plant Science Letters 38:53-59, 1985.

Harry, I. S. and T. A. Thorpe. Somatic embryogenesis and plant regeneration from mature zygotic embryos of red spruce. Botani Local Gazette 152:446-452, 1991.

Jain, S. M., N. Dong, and R. J. Newton. Somatic embryogenesis in slash pine (*Pinus elliottii*) from immature embryos cultured in vitro. Plant Science 65:233-241, 1989.

Kermode, A. R. and J. D. Bewley. The role of maturation drying in the transition from seed development to germination. Journal of Experimental Botany 36:1906-1915, December 1985.

Kermode, A. R., E. B. Dumbroff, and J. D. Bewley. The role of maturation drying in the transition from seed development to germination. Journal of Experimental Botany 40:303-313, February 1989.

Klimaszewska, K. Plantlet development from immature zygotic embryos of hybrid larch through somatic embryogenesis. Plant Science 63:95-103, 1989.

Klimaszewska, K., C. Ward, and W. M. Cheliak. Cryopreservation L 5 and plant regeneration from embryogenic cultures of larch (*Larix × eurolepis*) and black spruce (*Picea mariana*). Journal of Experimental Botany 43:73-79, January 1992.

Laine, E. and A. David. Somatic embryogenesis in immature embryos and protoplasts of *Pinus caribaea*. Plant Science 69:215-224, 1990.

Michler, C. H., T. M. Voelker, and R. Moioffer. Effects of embryo explant type and developmental maturity on eastern white pine (*Pinus strobus L.*) embryogenic callus initiation (Abstract). In: Applications of biotechnology to tree culture, protection and utilization. (eds Haissig et al.) Columbus, Ohio. Aug. 5-8, 1991. U.S.D.A. Forest Serv., Northeastern Forest Experiment Station, p. 117, 1991.

Owens, L. D. and C. A. Wozniak. Measurement and effects of gel matric potential and expressibility on production of morphogenic callus by cultured sugarbeet leaf discs. Plant Cell, Tissue and Organ Culture 26:127-133, 1991.

Preston, R. J. North American Trees 4th edition. Iowa State Univ. Press, Ames. pp. 4-7, 1989.

Pullman, G. S. and P. K. Gupta. Method for reproducing coniferous plants by somatic embryogenesis using adsorbent materials in the development stage media. U.S. Pat. No. 5,034,326—issued Jul. 23, 1991.

Roberts, D. R. Process for the production, desiccation and germination of conifer somatic embryos. U.S. Pat. No. 5,183,757—issued Feb. 2, 1993.

Schenk, R. U. and A. C. Hildebrandt. Medium and techniques for induction and growth of monocotyledonous and dicotyledonous plant cell cultures. Canadian Journal of Botany 50:199-204, 1972.

Smith, D. R., A. P. Singh, and L. Wilton, Zygotic embryos of *Pinus radiata* in vivo and in vitro. In: Smith DR (ed) Abstracts, Int Conifer tissue culture working group, 12-16 Aug. 1985. For Res Inst, N Z For Serv, Rotorua, New Zealand, 1985.

Tautorus, T. E., L. C. Fowke, and D. I. Dunstan. Somatic embryogenesis in conifers. Canadian Journal of Botany 69:1873-1899, 1991.

Teasdale, R. D., P. A. Dawson, and H. W. Woolhouse. Mineral nutrient requirements of a loblolly pine (*Pinus taeda*) cell suspension culture. Plant Physiology 82:942-945, 1986.

Tremblay, L. and F. M. Tremblay. Effects of gelling agents, ammonium nitrate, and light on the development of *Picea mariana* (Mill) B. S. P. (black spruce) and *Picea rubens* Sarg. (red spruce) somatic embryos. Plant Science 77: 233–242, 1991.

Uddin, M. Somatic embryogenesis in gymnosperms. U.S. Pat. No. 5,187,092—issued Feb. 16, 1993.

von Arnold, S. Improved efficiency of somatic embryogenesis in mature embryos of Picea abies (L.) Karst. Journal of Plant Physiology 128:233–244, 1987.

von Arnold, S. and I. Hakman. Regulation of somatic embryo development in Picea abies by abscisic acid (ABA). Journal of Plant Physiology 132:164–169, 1988.

Webster, F. B., D. R. Roberts, S. M. McInnis, and B. C. S. Sutton. Propagation of interior spruce by somatic embryogenesis. Canadian Journal of Forest Research 20:1759–1765, 1990.

What is claimed is:

1. A method for reproducing plants selected from the group consisting of *Pinus taeda, Pinus serotina, Pinus palustris, Pinus elliottii, Pinus rigida,* and hybrids thereof, by somatic embryogenesis which comprises:
   (a) placing a suitable explant selected from the group consisting of immature zygotic embryos and megagametophytes containing immature zygotic embryo on culture initiation medium containing a sufficient amount of nutrients, 0.1 to 5.0 mg/l of auxin, 0.1 to 1.0 mg/l of cytokinin, about 30.0 g/l of sucrose, and a level of gelling agent selected from the group consisting of 2.5 to 4.5 g/l of agar, 0.5 to 1.5 g/l of gellan gum, 3.0 to 5.0 g/l of agarose, and 1.5 to 3.0 g/l of AGARGEL, for 2 to 14 weeks under suitable environmental conditions to grow a culture containing embryogenic tissue;
   (b) transferring the embryogenic tissue culture to culture maintenance medium containing a sufficient amount of nutrients, 0.1 to 5.0 m/l of auxin, 0.1 to 1.0 mg/l of cytokinin, about 30.0 g/l of sucrose, and a level of gelling agent selected from the group consisting of 6.0 to 9.0 g/1 of agar, 1.75 to 3.50 g/l of gellan gum, 6.0 to 8.0 g/l of agarose, and 3.5 to 5.0 g/l of AGARGEL, for a sufficient time under suitable environmental conditions to develop a mass of embryogenic tissue having a minimum weight of at least 100 mg;
   (c) transferring at least 100 mg of the mass of embryogenic tissue to embryo development medium containing a sufficient amount of nutrients, 5.0 to 33.0 mg/l of abscisic acid, a level of gelling agent selected from the group consisting of 6.0 to 12.0 g/l of agar, 1.75 to 4.00 g/l of gellan gum, 6.0 to 8.0 g/l of agarose, and 3.5 to 6.0 g/l of AGARGEL, and 20.0 to 70.0 g/l of a sugar selected from the group consisting of glucose, maltose, sucrose, and combinations thereof, for a sufficient time under suitable environmental conditions to develop stage 3 somatic embryos;
   (d) separating the stage 3 somatic embryos from the development medium and partially drying the embryos by exposing the embryos to an atmosphere having a high relative humidity for sufficient time to permit the embryos to lose about 25% to 75% of their pre-dried weight;
   (e) transferring the partially dried somatic embryos to germination medium containing a sufficient amount of nutrients, a level of gelling agent selected from the group consisting of 6.0 to 9.0 g/l of agar, 1.75 to 3.50 g/l of gellan gum, 6.0 to 8.0 g/l of agarose, and 3.5 to 5.0 g/l of AGARGEL, and 20.0 to 40.0 g/l of a sugar selected from the group consisting of glucose, maltose, sucrose, and combinations thereof for a sufficient time under suitable environmental conditions to germinate the partially dried embryos;
   (f) converting the germinated embryos into acclimatized plants; and
   (g) field planting the acclimatized plants.

2. The method of claim 1 wherein said Pinus interspecies hybrid plant is selected from the group consisting of *Pinus rigida* × *Pinus taeda, Pinus taeda* × *Pinus rigida, Pinus serotina* × *Pinus taeda,* and *Pinus taeda* × *Pinus serotina.*

3. The method of claim 1 wherein said culture initiation medium contains a level of gelling agent selected from the group consisting of 3.0 to 4.0 g/l of agar, 0.75 to 1.25 g/l of gellan gum, 3.5 to 4.5 g/l of agarose, and 1.75 to 2.50 g/l of AGARGEL.

4. The method of claim 1 wherein the explant is placed on culture initiation medium for a period of time of 3 to 10 weeks.

5. The method of claim 1 wherein the embryogenic tissue culture is placed on culture maintenance medium for a period of 1 to 14 weeks.

6. The method of claim 1 wherein the embryogenic tissue culture has been cryopreserved.

7. The method of claim 1 wherein the mass of embryogenic tissue is placed on embryo development medium for a period of 3 to 18 weeks.

8. The method of claim 1 wherein at least 200 mg of the mass of embryogenic tissue is placed on embryo development medium.

9. The method of claim 1 wherein the embryo development medium contains from 11.0 to 27.0 mg/l of abscisic acid.

10. The method of claim 1 wherein the mass of embryogenic tissue on the embryo development medium is cultured in a dark environment.

11. The method of claim 1 wherein the embryo development medium has an osmolality level in the range of about 120 to 330 mM/kg.

12. The method of claim 1 wherein the stage 3 somatic embryos are partially dried for a period of 2 to 6 weeks.

13. The method of claim 1 wherein the stage 3 somatic embryos are partially dried by exposing the embryos to an atmosphere having from greater than 90% up to 99% humidity for sufficient time to permit the embryos to lose from about 25% to 75% of their pre-dried weight.

14. The method of claim 1 wherein the partially dried somatic embryos are placed on germination medium for a period of 1 to 8 weeks.

15. The method of claim 1 wherein the germination medium contains from 1.0 to 10.0 g/l of activated carbon.

16. The method of claim 1 wherein the germination medium contains a nutrient nitrogen source selected from the group consisting of L-glutamine, ammonium nitrate, and combinations thereof.

17. The method of claim 1 wherein the germination medium contains from 0.75 to 4.50 g/l of L-glutamine as a nutrient nitrogen source.

18. The method of claim 1 wherein the germination medium contains from 0.75 to 1.50 g/l of L-glutamine as a nutrient nitrogen source.

19. The method of claim 1 wherein the germination medium contains from 0.4 to 2.4 g/l of ammonium nitrate as a nutrient nitrogen source.

20. The method of claim 1 wherein the germination medium contains from 0.4 to 1.0 g/l of ammonium nitrate as a nutrient nitrogen source.

21. The method of claim 15 wherein the germination medium contains a nutrient nitrogen source selected from the group consisting of L-glutamine, ammonium nitrate, and combinations thereof.

22. The method of claim 15 wherein the germination medium contains from 0.75 to 4.50 g/l of L-glutamine as a nutrient nitrogen source.

23. The method of claim 15 wherein the germination medium contains from 0.75 to 1.50 g/l of L-glutamine as a nutrient nitrogen source.

24. The method of claim 15 wherein the germination medium contains from 0.4 to 2.4 g/l of ammonium nitrate as a nutrient nitrogen source.

25. The method of claim 15 wherein the germination medium contains from 0.4 to 1.0 g/l of ammonium nitrate as a nutrient nitrogen source.

26. The method of claim 1 wherein at least 100 mg of the mass of embryogenic tissue is transferred to embryo predevelopment medium having an osmolality level in the range of about 120 to 180 mM/kg and containing a sufficient amount of nutrients, a level of gelling agent selected from the group consisting of 6.0 to 9.0 g/l of agar, 1.75 to 3.50 g/l of gellan gum, 6.0 to 8.0 g/l of agarose, and 3.5 to 5.0 g/l of AGARGEL, 1.0 to 10.0 g/l of activated carbon, and 20.0 to 35.0 g/l of a sugar selected from the group consisting of glucose, maltose, sucrose, and combinations thereof, for a period of time of about 1 to 21 days under suitable environmental conditions to maintain the mass of embryogenic tissue prior to the mass being transferred to embryo-development medium.

27. The method of claim 26 wherein at least 200 mg of the mass of embryogenic tissue is transferred to embryo predevelopment medium.

28. The method of claim 1 wherein the explant is placed onto a sterile permeable membrane which has been placed on the surface of the culture initiation medium.

29. The method of claim 1 wherein the embryogenic tissue culture is transferred onto a sterile permeable membrane which has been placed on the surface of the culture maintenance medium.

30. The method of claim 1 wherein the mass of embryogenic tissue culture is transferred onto a sterile permeable membrane which has been placed on the surface of the embryo development medium.

31. The method of claim 1 wherein the partially dried somatic embryos are transferred onto a sterile permeable membrane which has been placed on the surface of the germination medium.

32. The method of claim 26 wherein the mass of embryogenic tissue culture is transferred onto a sterile permeable membrane which has been placed on the surface of the embryo predevelopment medium.

* * * * *

UNITED STATES PATENT AND TRADEMARK OFFICE
CERTIFICATE OF CORRECTION

PATENT NO. : 5,413,930
DATED : May 9, 1995
INVENTOR(S) : Michael R. Becwar; Emily E. Chesick; Levis W. Handley III; and Mark R. Rutter It is certified that error appears in the above-indentified patent and that said Letters Patent is hereby corrected as shown below:

In column 4, line 15, delete "he", and substitute therefor --the--.

In column 5, line 51, delete "agaro", and substitute therefor --agar.--.

In column 10, line 21, in Table II, delete "$KSG_2$" in the Development medium column and "$KSG_3$" in the Germination medium column, and substitute therefor --$MSG_2$-- in the Development medium column, and substitute therefor --$MSG_3$-- in the Germination medium column.

In column 10, line 28, in Table II, delete "Maltese", and substitute therefor --Maltose--.

In column 10, in Table II, insert a heading after the Activated carbon row and before the $Auxin_b$ row entitled --CONCENTRATION, mg/l--.

UNITED STATES PATENT AND TRADEMARK OFFICE
CERTIFICATE OF CORRECTION

PATENT NO. : 5,413,930
DATED : May 9, 1995
INVENTOR(S) : Michael R. Becwar; Emily E. Chesick; Levis W. Handley III; and Mark R. Rutter It is certified that error appears in the above-indentified patent and that said Letters Patent is hereby corrected as shown below:

In column 15, line 36, delete "checked-by", and substitute therefor --checked by--.

In column 17, line 16, in Table V, after Gelling, insert --Agents--.

In column 17, line 26, in Table V, delete "DCR", and substitute therefor --$DCR_1$--.

In column 17, line 68, delete "DCR", and substitute therefor --$DCR_1$--.

In column 19, line 1, delete "MSG", and substitute therefore --$MSG_1$--.

In column 19, line 9, insert a period --.-- after development.

In column 19, line 9, delete "out", and substitute therefor --About--.

In column 19, line 23, delete "DCR", and substitute therefor --$DCR_1$--.

UNITED STATES PATENT AND TRADEMARK OFFICE
CERTIFICATE OF CORRECTION

PATENT NO. : 5,413,930
DATED : May 9, 1995
INVENTOR(S) : Michael R. Becwar; Emily E. Chesick; Levis W. Handley III; and Mark R. Rutter It is certified that error appears in the above-indentified patent and that said Letters Patent is hereby corrected as shown below:

In column 19, line 45, insert between from and different --3--.

In column 20, line 22, delete "MSG]", and substitute therefor --$MSG_3$--.

In column 20, line 36, delete "30".

In column 21, line 11, delete 78 g/m, and substitute therefor --78 $g/m^3$--.

In column 23, line 3, in Table VIII, delete "rislida", and substitute therefor --rigida--.

In column 23, line 15, in Table VIII, in footnote c, delete "rigids", and substitute therefor --rigida--.

In column 23, line 51, delete ",".

In column 24, line 1, delete "F", and substitute therefore --$F_1$--.

In column 24, line 56, delete "DCR", and substitute therefor --$DCR_1$--.

In column 25, line 28, insert --24-- between of and cultures.

In column 25, line 64, delete "MSG", and substitute therefor --$MSG_1$--.

In column 25, line 68, delete "XI", and substitute therefor --X--.

UNITED STATES PATENT AND TRADEMARK OFFICE
CERTIFICATE OF CORRECTION

PATENT NO. : 5,413,930
DATED : May 9, 1995
INVENTOR(S) : Michael R. Becwar; Emily E. Chesick; Levis W. Handley III; and Mark R. Rutter It is certified that error appears in the above-indentified patent and that said Letters Patent is hereby corrected as shown below:

In column 26, line 12, in Table X, insert footnote a as follows: --[a]Each piece of ET was approximately 200 mg.

In column 26, line 52, delete "DCR", and substitute therefor --$DCR_1$--.

In column 27, line 15, delete XII, and substitute therefor --XI--.

In column 27, line 42, in Table XI, in the footnotes, the second line is part of Footnote [a], insert a --[b]-- prior to ET at the third line.

In column 29, line 53, in Table XIII, delete "$KSG_3$", and substitute therefor --$MSG_3$--.

In column 29, line 65, delete "MSG", and substitute therefor --$MSG_3$--.

In column 30, line 40, in Table XIV, delete "(5%)", and substitute therefor --(54)--.

In column 30, line 42, in Table XIV, delete "(4%)", and substitute therefor --(44)--.

In column 32, line 5, delete "Botani Local", and substitute therefor --Botanical--.

UNITED STATES PATENT AND TRADEMARK OFFICE
CERTIFICATE OF CORRECTION

PATENT NO. : 5,413,930
DATED : May 9, 1995
INVENTOR(S) : Michael R. Becwar; Emily E. Chesick; Levis W. Handley III; and Mark R. Rutter It is certified that error appears in the above-indentified patent and that said Letters Patent is hereby corrected as shown below:

In column 32, line 24, delete "L 5".

In column 33, lines 26 and 27, delete "embryo", and substitute therefor --embryos--.

Signed and Sealed this

Eighth Day of August, 1995

Attest:

BRUCE LEHMAN

Attesting Officer

Commissioner of Patents and Trademarks